(12) United States Patent
Rolfes et al.

(10) Patent No.: US 8,790,701 B2
(45) Date of Patent: Jul. 29, 2014

(54) POLY-α(1→4)GLUCOPYRANOSE-BASED MATRICES WITH HYDRAZIDE CROSSLINKING

(75) Inventors: Emily R. Rolfes, Eden Priarie, MN (US); Jeff J. Ross, Chaska, MN (US); Joseph S. McGonigle, Minneapolis, MN (US); Gary W. Opperman, St. Louis Park, MN (US); Stephen J. Chudzik, St. Paul, MN (US); Pamela J. Reed, legal representative, St. Paul, MN (US)

(73) Assignee: SurModics, Inc., Eden Prairie, MN (US)

( * ) Notice: Subject to any disclaimer, the term of this patent is extended or adjusted under 35 U.S.C. 154(b) by 632 days.

(21) Appl. No.: 12/387,046

(22) Filed: Apr. 27, 2009

(65) Prior Publication Data

US 2009/0269407 A1 Oct. 29, 2009

Related U.S. Application Data

(60) Provisional application No. 61/125,712, filed on Apr. 28, 2008.

(51) Int. Cl.
*A61K 9/14* (2006.01)
*A61F 2/00* (2006.01)

(52) U.S. Cl.
USPC .............................. 424/488; 424/484; 424/426

(58) Field of Classification Search
CPC ... A61K 47/4823; A61K 47/36; A61K 47/38; A61I 26/0023; C08B 31/006; C08B 31/185
USPC .......................................... 424/488, 484, 426
See application file for complete search history.

(56) References Cited

U.S. PATENT DOCUMENTS

| | | | |
|---|---|---|---|
| 4,788,280 A | 11/1988 | Billmers et al. | |
| 5,529,914 A | 6/1996 | Hubbell et al. | |
| 5,854,382 A | 12/1998 | Loomis | |
| 6,007,833 A | 12/1999 | Chudzik et al. | |
| 6,040,295 A * | 3/2000 | Rolland et al. | 514/44 R |
| 6,051,248 A | 4/2000 | Sawhney et al. | |
| 6,153,211 A | 11/2000 | Hubbell et al. | |
| 6,316,522 B1 | 11/2001 | Loomis et al. | |
| 6,642,363 B1 | 11/2003 | Mooney et al. | |
| 6,790,840 B1 | 9/2004 | Lee et al. | |
| 6,818,018 B1 | 11/2004 | Sawhney | |
| 7,070,809 B2 | 7/2006 | Goupil et al. | |
| 8,039,447 B2 | 10/2011 | Rinaudo et al. | |
| 2004/0028745 A1 | 2/2004 | Bouhadir et al. | |
| 2005/0255142 A1 | 11/2005 | Chudzik et al. | |
| 2006/0019877 A1 | 1/2006 | Conradt et al. | |
| 2007/0065483 A1 | 3/2007 | Chudzik et al. | |
| 2007/0065484 A1 | 3/2007 | Chudzik et al. | |
| 2007/0071792 A1 | 3/2007 | Varner et al. | |
| 2009/0093550 A1 | 4/2009 | Rolfes et al. | |

FOREIGN PATENT DOCUMENTS

| | | |
|---|---|---|
| WO | WO 02/06373 | 2/2002 |
| WO | WO 2004/050712 | 6/2004 |
| WO | WO 2004/098503 | 11/2004 |
| WO | WO 2006/001046 | 1/2006 |
| WO | WO 2007/102149 | 9/2007 |
| WO | WO 2007/120818 | 10/2007 |

OTHER PUBLICATIONS

Wermuth, Drug Discovery Today, 2006, 11(7/8), 348-354.*
Bioconjugate Techniques, 1996, Academic Press, pp. 3-166.*
PCT Search Report for International Application No. PCT/US2009/002567 mailed on Dec. 8, 2009.

* cited by examiner

*Primary Examiner* — Abigail Fisher
(74) *Attorney, Agent, or Firm* — Kagan Binder, PLLC

(57) ABSTRACT

The present invention provides biocompatible, biodegradable matrices formed from poly-α(1→4)glucopyranose and reactive hydrazide groups. The matrices can be used for various applications in the body, including drug delivery and cell therapy.

27 Claims, 10 Drawing Sheets

Plasmid DNA release from maltodextrin matrices siRNA release from maltodextrin matrices

Release of plasmid DNA from maltodextrin matrices

Release of polyplexed DNA from maltodextrin matrices

Each data point represents the mean for n = 3 samples

```
                     SEQUENCE LISTING

<160> NUMBER OF SEQ ID NOS: 13

<210> SEQ ID NO 1
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 1

Tyr Ile Gly Ser Arg
1               5

<210> SEQ ID NO 2
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 2

Asp Gly Glu Ala
1

<210> SEQ ID NO 3
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 3

Leu Arg Gly Asp Asn
1               5

<210> SEQ ID NO 4
```

```
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 4

Ile Lys Val Ala Val
1               5

<210> SEQ ID NO 5
<211> LENGTH: 5
<212> TYPE: PRT
<213> ORGANISM: Artificial Sequence
<220> FEATURE:
<223> OTHER INFORMATION: chemically synthesized peptide

<400> SEQUENCE: 5

Pro Asp Ser Gly Arg
1               5

<210> SEQ ID NO 6
<211> LENGTH: 10
<212> TYPE: PRT
<213> ORGANISM: Artificial Sequence
<220> FEATURE:
<223> OTHER INFORMATION: chemically synthesized peptide

<400> SEQUENCE: 6

Arg Asn Ile Ala Glu Ile Ile Lys Asp Ala
1               5                   10

<210> SEQ ID NO 7
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 7

Arg Gly Asp Ser
1

<210> SEQ ID NO 8
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 8

Arg Gly Asp Thr
1

<210> SEQ ID NO 9
<211> LENGTH: 4
<212> TYPE: PRT
<213> ORGANISM: Artificial Sequence
<220> FEATURE:
<223> OTHER INFORMATION: chemically synthesized peptide

<400> SEQUENCE: 9

Arg Gly Asp Val
1

<210> SEQ ID NO 10
<211> LENGTH: 4
```

```
<212> TYPE: PRT
<213> ORGANISM: Artificial Sequence
<220> FEATURE:
<223> OTHER INFORMATION: chemically synthesized peptide

<400> SEQUENCE: 10

Arg Glu Asp Val
1

<210> SEQ ID NO 11
<211> LENGTH: 15
<212> TYPE: PRT
<213> ORGANISM: Artificial Sequence
<220> FEATURE:
<223> OTHER INFORMATION: chemically synthesized peptide

<400> SEQUENCE: 11

Gly Thr Pro Gly Pro Gln Gly Ile Ala Gly Gln Arg Gly Val Val
1               5                   10                  15

<210> SEQ ID NO 12
<211> LENGTH: 4
<212> TYPE: PRT
<213> ORGANISM: Artificial Sequence
<220> FEATURE:
<223> OTHER INFORMATION: chemically synthesized peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Val Thr Xaa Gly
1

<210> SEQ ID NO 13
<211> LENGTH: 7
<212> TYPE: PRT
<213> ORGANISM: Artificial Sequence
<220> FEATURE:
<223> OTHER INFORMATION: chemically synthesized peptide

<400> SEQUENCE: 13

Phe Tyr Val Val Met Trp Lys
1               5
```

POLY-α(1→4)GLUCOPYRANOSE-BASED MATRICES WITH HYDRAZIDE CROSSLINKING

CROSS-REFERENCE TO RELATED APPLICATION

This application claims the benefit of U.S. Provisional Patent Application Ser. No. 61/125,712, filed Apr. 28, 2008, entitled Low Molecular Weight Poly-α(1-4)Glucopyranose-Based Matrices with Hydrazide Crosslinking, the disclosure of which is incorporated herein by reference. Also, the entire contents of the ASCII text file entitled "SRM0116USSequenceListing_ST25.txt" created on Nov. 5, 2012, having a size of 3 kilobytes is incorporated herein by reference.

FIELD OF THE INVENTION

The present invention is directed to biocompatible, biodegradable matrices for use in the body. The matrices can include a cellular material and can be used in vivo as cell scaffolds, or can include a therapeutic compound, which can be released from the matrix.

BACKGROUND

Polymeric hydrogel matrices have been described as biomaterials useful for the treatment of a variety of medical conditions. (See, for example, U.S. Pat. Nos. 5,529,914, 5,854,382, 6,007,833, 6,051,248, 6,153,211, 6,316,522, 6,818,018, and 7,070,809.) Depending on the polymeric material used, these matrices may be biostable, or biodegradable following a period of implantation. The polymeric material used to form these matrices is desirably biocompatible, meaning that it does not have an adverse biological effect on the organism in which the hydrogels are placed or formed. Accordingly, it is generally desirable to avoid the use of biodegradable materials that degrade into products that cause unwanted side effects in the body by virtue of their presence or concentration in vivo. These unwanted side effects can include immune reactions, toxic buildup of the degradation products in the liver, or the initiation or provocation of other adverse effects on cells or tissue in the body.

The ability of the hydrogel matrices to provide a positive effect for the treatment of a subject may occur by the structural and chemical properties of the hydrogel matrices mimicking the natural tissue and facilitating tissue healing. Hydrogel matrices may also exert a protective affect to tissues, thereby preventing tissue or cellular damage (for example in the case of an inflammatory response).

In some cases, hydrogel matrices may be associated with a drug that is designed to provide a therapeutic effect to tissue at the site the hydrogel is localized or formed. For example, it has been proposed to use a drug that is released from the matrix by diffusion, or released by the degradation of the hydrogel matrix, for treatment of a target tissue.

Hydrogel matrices have been proposed for medical use in a variety of forms. In some cases, hydrogel matrices can be formed as tissue-healing articles on a wound site, designed to promote tissue regeneration and healing of the wound. When applied this way, these hydrogel matrices are amorphous and typically conform to the tissue on which the hydrogel matrix-forming composition is applied. These matrices can be formed in situ, such as by the application of the matrix-forming composition on the treatment site and the treatment of the composition to cause crosslinking of the hydrogel forming material.

In other cases, hydrogel matrices can be formed in association with an implantable medical device. In these cases, the matrices may have a more distinct form, such as a coating on the surface of a device, or a fill that conforms to a void in the device.

Many challenges remain for the formation and use of hydrogel matrices as in situ formed articles, or in association with implantable medical devices.

In the case of biodegradable matrices, one challenge relates to the preparation of matrices having suitable degradation properties in vivo. For example, some natural polymers, such as hyaluronic acid and alginic acid, are biodegradable in polymeric form, but can be crosslinked to form non-biodegradable hydrogel matrices. On the other hand, hydrogel matrices formed from polymeric materials with a significant amount of ester linkages will typically degrade by bulk erosion. The bulk erosion may cause the matrices to degrade too rapidly and/or without control. This may cause matrix fragmentation resulting in the undesirable loss of embolic matrix fragments into the circulatory system.

In addition, many hydrogel matrices lack desirable physical properties, such as sufficient durability for implantable procedures, or controlled swelling. For example, matrices that are highly hydrophilic can rapidly absorb water and cause plasticization of the polymer, resulting in a soft gel-like matrix. This characteristic is undesirable as the matrix can tear upon expansion and ruin its physical integrity.

Some hydrogels of the prior art rely on chemical agents to cure the polymeric materials. Many of these chemical agents are small compounds that can cause tissue damage, and are therefore undesirably used in the body.

In addition, hydrogel matrices that are designed for drug release are generally not well developed. Hydrogel matrices intended to release a therapeutic agent have been problematic because release is typically inadequately controlled. For example, in many cases, the majority of the agent is released from the matrix in a short burst, resulting in depletion of the agent from the hydrogel matrices. This burst is particularly undesirable when a therapeutic effect is required over an extended period of time. The short term burst is thought to be caused by the hydrophilicity of the polymeric materials driving water into the matrix, causing an increase in the osmotic pressure in the coating. As a result, the permeability of the matrix for the drug is significantly increased, resulting in the elution of the drug at a therapeutically ineffective rate.

In addition, certain polymeric materials, reagents, and/or methods of preparing hydrogels may be incompatible with or unsuitable for certain therapeutic agents. For example, in technologies using polymeric macromers, hydrogel formation is typically carried out using a free radical-generating system. Unfortunately, free radicals can be damaging to many macromolecules, such as nucleic acids, and even cells. Also, the use of polymers with an abundance of charged groups as hydrogel forming materials may attract oppositely charged therapeutic agents and alter their release from the gel. Alternatively, matrices formed from highly charged polymers and including cellular material may cause undesirable cellular responses in the cells.

Embodiments of the present invention address one or more of these problems associated with hydrogel technologies of the prior art.

SUMMARY

The present invention is directed to biocompatible, biodegradable matrices that can be used in the body, such as for the treatment of a medical condition. The matrices are formed from a polysaccharide-based material that can be crosslinked under mild conditions, which, under some embodiments of the invention, is particularly suitable for the entrapment of sensitive biological materials, such as cells and therapeutic macromolecules. In particular, the matrices are formed from a polymeric material comprising a poly-α(1→4)glucopyranose, and reactive hydrazide groups, which are used to form the linking groups of the crosslinked matrix. The matrix can be formed without using low molecular weight crosslinking components or activators that lack biocompatibility or that are potentially toxic to an organism. Microparticles including bioactive agent can optionally be included in the matrix.

The matrices formed using these polymeric materials and reactive hydrazide chemistries have desirable physical properties for use in vivo, such as durability, limited swellability, in vivo biodegradability, and biocompatibility.

In one aspect, the invention provides a biodegradable, biocompatible crosslinked polymeric matrix including polymeric segments that comprise poly-α(1→4)gluco-pyranose. The polymeric segments including poly-α(1→4)glucopyranose are crosslinked together with linker segments including a chemistry selected from:

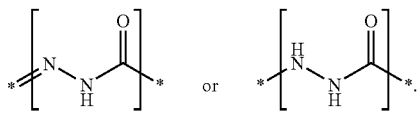

The amine or carbonyl groups, or both, of these chemistries can be directly bonded to a portion of the polymeric material forming the matrix, or can be a portion of a larger linker with additional atoms. In some aspects, the matrix is formed from a poly-α(1→4)glucopyranose having a molecular weight of 500,000 Da or less.

Optionally, the matrix can include, in addition to the poly-α(1→4)glucopyranose, a matrix-forming component that is different than the polymeric segment comprising poly-α(1→4)glucopyranose. For example, in some cases, the matrix includes a matrix-forming component that comprises a synthetic hydrophilic polymer or a polypeptide.

In some cases, the linker segments are formed of reacted hydrazide groups pendent from the polymeric segments or component, the linker segments also including ester groups. When used in vivo, degradation of the matrix can occur through enzymatic degradation of the segments including poly-α(1→4)glucopyranose, as well as through non-enzymatic hydrolytic cleavage of the ester groups. The presence of ester groups in the linker segments can increase the rate of degradation of the matrix. In some aspects of the invention, a portion of the linker segments includes ester groups.

In another aspect, the invention provides a system for forming a biodegradable, biocompatible crosslinked polymeric matrix. The system includes an α(1→4)glucopyranose polymer that has pendent first reactive groups. The system also includes a second polymer having second reactive groups. The first reactive groups are reactive with the second reactive groups, with either the first or second reactive groups including a hydrazide group, and the corresponding reactive group including a hydrazide reactive group. Also, the first reactive groups have a degree of substitution on the α(1→4)glucopyranose polymer in the range of 0.05 to about 1.0. The second polymer having second reactive groups can be an α(1→4) glucopyranose polymer or a component that is different that an α(1→4)glucopyranose polymer.

The invention also provides a method for preparing a biodegradable, biocompatible crosslinked polymeric matrix. The method includes the steps of providing a first composition comprising poly-α(1→4)glucopyranose having pendent hydrazide groups or hydrazide-reactive groups, and also providing a second composition comprising a matrix-forming component that is the same or different than the poly-α(1→4) glucopyranose, the matrix-forming component including pendent hydrazide groups or hydrazide-reactive groups. The pendent groups of the poly-α(1→4)glucopyranose and the matrix-forming component are reacted to form a biodegradable, biocompatible crosslinked polymeric matrix. In some aspects, the poly-α(1→4)glucopyranose has a molecular weight of weight of 500,000 Da or less.

In some embodiments, the matrix includes a bioactive agent, and is capable of releasing the bioactive agent when the matrix is placed or formed in the body. The bioactive agent-containing matrix can be in form of an implantable article, or can be associated with an implantable device, such as in the form of a coating on a surface of a device, or as a filler in a portion of the device.

In related aspects, the invention provides a method for treatment of a subject. The method includes forming or placing in the body a biodegradable matrix of the invention, the matrix including a bioactive agent, a bioparticle, or both. After forming or placing the matrix in the body, the matrix degrades and releases the bioactive agent to the subject. One or more bioactive agent(s) or bioparticle(s) can be selected and included in the matrix for the treatment of a condition.

In some aspects the biodegradable matrix can include a bioactive agent that is a macromolecule, such as a polypeptide, polysaccharide, or polynucleotide. The matrix can include bioparticles, such as viral particles, and cells, such as prokaryotic cells and eukaryotic cells.

In some embodiments, the matrices of the invention are used in a gene therapy method in a subject. The method involves the release of a polynucleotide from the matrix that acts on a tissue or cell to produce a biological effect. In some aspects, the polynucleotide is used to treat a disease by reducing the expression of a gene encoding a target protein. The polynucleotide can also be in a particulate in the matrix, such as a viral vector, or in a microparticle.

Formation of the matrices can be carried out using mild conditions that are favorable to sensitive biomaterials, such as macromolecules, and also bioparticles, which include cells. For example, the methods of the invention allow formation of the crosslinked matrix without subjecting the materials to conditions of high heat or pH extremes. The use of radical components or oxidants which can damage macromolecules and bioparticles, can also be avoided. For example, the polymeric matrix-forming materials can be reacted to form a matrix without using low molecular weight crosslinking components or activators that lack biocompatibility or that are potentially toxic to an organism.

In many embodiments, since the matrix is at least partially formed from polymeric segments including poly-α(1→4) glucopyranose, degradation of the matrix in vivo can primarily occur by enzymatic degradation of the poly-α(1→4) glucopyranose on the surface of the matrix. The resulting surface erosion of the matrix material, as caused by the enzymatic activity, can cause release of bioactive agent or a bioparticle coinciding with polysaccharide degradation. In these cases, little or no loss of bioactive agent occurs by diffusion of the bioactive agent out of the intact matrix. In other cases, a matrix can be prepared with a bioactive agent that can diffuse out of the matrix prior to matrix degradation.

Given the physical and chemical properties of the matrix, the bioactive agent can be released from the matrix at therapeutically desirable rates. Experimental results associated with the invention showed that the matrices can release bioactive agent at a steady, therapeutically effective rate. This allows the matrices to be useful for the prolonged release of bioactive agents to treat medical conditions.

In some embodiments, the matrix is in the form of a cell scaffolding. In these embodiments, the matrices of the present invention, and the methods used to form them, have been found to be neutral towards cells and do not cause undesirable cellular responses, or result in decreases in overall cell viability. The matrices can readily be modified to provide a desired microenvironment for the maintenance of cells within the matrix. In some cases, the matrix can be prepared using cellular adhesion factors which can provide points for the cells to attach to within the framework of the polysaccharide matrix. Cellular adhesion factors, such as matrix proteins and portions thereof, can be reacted with portions of the matrix material to modify the polysaccharide matrix.

Accordingly, the invention provides a cell scaffolding comprising a biodegradable, biocompatible crosslinked polymeric matrix comprising polymeric segments comprising poly-α(1→4)glucopyranose, with linker segments including a chemistry selected from:

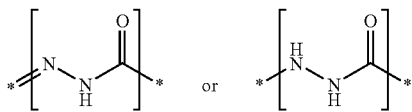

wherein the linker segments crosslink the polymeric segment and matrix-forming component. In some cases the polymeric segments comprising poly-α(1→4)glucopyranose have a molecular weight of 500,000 Da or less.

Optionally, the matrix can include, in addition to the poly-α(1→4)glucopyranose, a matrix-forming component that is different than the polymeric segment comprising poly-α(1→4)glucopyranose. The matrix also comprises cells, and is capable of degrading in vivo.

The matrices and cell scaffoldings of the present invention can be used in a method for the treatment of a subject. The method includes forming or placing in the body a biodegradable cell scaffolding, which includes the matrix components of the invention, and the cell scaffolding includes cells. The cell scaffolding can provide a therapeutic effect to the subject in one or more ways. In the case of tissue damage, the cell scaffolding can promote more favorable tissue remodeling. For example, factors produced by the cells in the matrix can be released and positively affect the damaged tissue to promote tissue healing. As another example, following contact with the damaged tissue, the cell scaffolding can degrade and provide a source of cells beneficial for tissue reconstruction.

In one particular example, the cell scaffolding is placed in contact with cardiovascular tissue. Cardiovascular tissue that can be treated may be tissue damaged in an invasive procedure, such as surgery, or damaged from an ischemic event.

Experimental results associated with the invention showed that poly-α(1→4)glucopyranose reagents reacted in the presence of cells not only were non-damaging to the cells, but were also able to maintain the viability of cells that were included in the matrix. This is desirable for using the matrices as vehicles for cellular therapy. In addition, matrices were formulated which also allowed cells to proliferate under the appropriate conditions.

The biodegradable matrix materials were amenable to modification with cell attachment factors, and these modifications were shown to have a desired, positive impact on cell viability, cell function, and/or retention.

DETAILED DESCRIPTION

Figure 1:
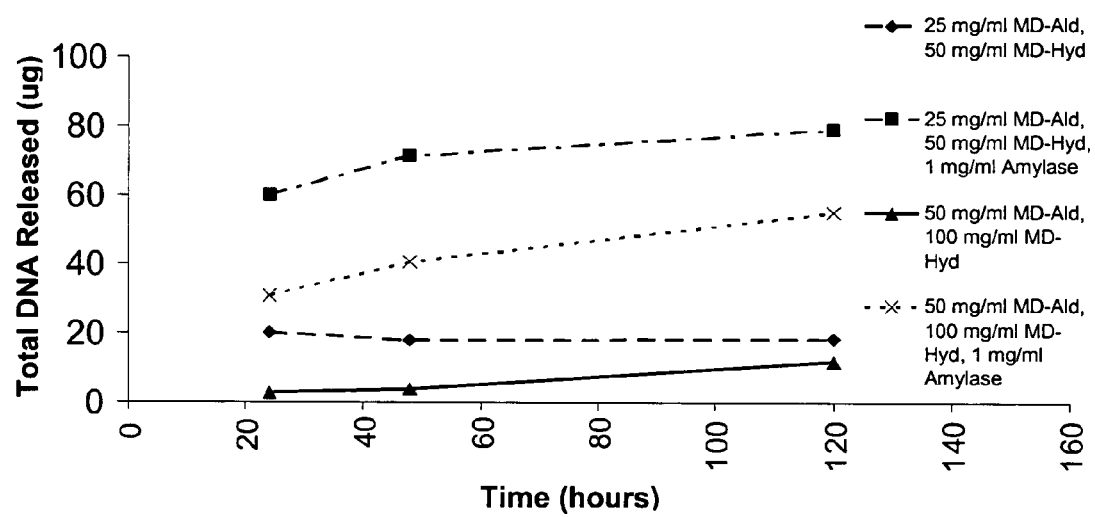
FIG. 1 is a graph showing release of plasmid DNA from maltodextrin-based matrices over time.

The embodiments of the present invention described herein are not intended to be exhaustive or to limit the invention to the precise forms disclosed in the following detailed description. Rather, the embodiments are chosen and described so that others skilled in the art can appreciate and understand the principles and practices of the present invention.

All publications and patents mentioned herein are hereby incorporated by reference. The publications and patents disclosed herein are provided solely for their disclosure. Nothing herein is to be construed as an admission that the inventors are not entitled to antedate any publication and/or patent, including any publication and/or patent cited herein.

As used herein, a "matrix" refers to a composition of crosslinked materials. Generally, when the matrix-forming materials are crosslinked, the composition that includes these materials transitions from a liquid state to a gel state, thereby forming a "gel" or a "gelled composition." The gel can have certain viscoelastic and rheological properties that provide it with certain degrees of durability and swellability.

Materials of the invention can be crosslinked to provide a matrix in a particular form useful for a medical or therapeutic application. Exemplary matrix forms include those of a coating on a surface of an implantable medical device, a three-dimensional implantable medical article formed of the crosslinked material, a cell scaffolding, a sealant, and an embolic composition.

Biodegradable matrix materials of the invention are useful in a variety of applications such as to make implantable medical devices (e.g., stents, tubes, aneurysm coils), in-situ delivery articles (e.g., cell delivery or bioactive agent delivery articles), and may also be used as tissue sealants.

The matrices can also be degradable in the body. As used herein the term "degradable" or "biodegradable" refers to matrix materials that are (1) hydrolytically degradable, (2) enzymatically degradable, or (3) both hydrolytically and enzymatically degradable. As used herein the term "hydrolytically degradable" refers to matrix materials that are degradable by hydrolysis reactions. As used herein the term "enzymatically degradable" refers to matrix materials that are degradable in the presence of an enzyme that specifically cleave regions of the particular polymeric material that is used to prepare the matrix. An enzymatically degradable matrix may be generally non-enzymatically hydrolytically stable, meaning that in the absence of an enzyme capable of degrading the matrix, the matrix will not degrade by simple hydrolysis.

In one aspect, the present invention provides a biodegradable, biocompatible crosslinked polymeric matrix having polymeric segments and linker segments. A segment of the polymeric matrix refers to the chemical material of a portion of the polymeric matrix. A portion of the material making up the matrix is poly-α(1→4)glucopyranose. Another portion of the material making up the matrix is linker segments. The linker segments generally refer to the chemical material linking one poly-α(1→4)glucopyranose-containing segment to another poly-α(1→4)glucopyranose-containing segment, or one poly-α(1→4)glucopyranose-containing segment to a matrix material that is different than the poly-α(1→4)glucopyranose-containing segment, such as another segment that includes polymeric material, or a non-polymeric material.

In some modes of practice, the matrix can be formed by the reaction of a α(1→4)glucopyranose polymer including a pendent first reactive group, with a second component that includes a second reactive group that is reactive with the first reactive groups. One of the first or second reactive groups includes a hydrazide group. For example, the α(1→4)glucopyranose polymer can include a pendent hydrazide group. The second component can be α(1→4)glucopyranose polymer, or a component that is different that the α(1→4)glucopyranose polymer, wherein the second component includes a group that is reactive with the hydrazide group. Exemplary hydrazide-reactive groups include aldehyde, acyl halides, NHS-esters, carboxylic acids, imido-esters, hydroxyl methyl phosphine, imidazoles, and unsaturated esters.

The α(1→4)glucopyranose polymers include repeating monomeric α-D-glucopyranose ($Glc_p$) having α(1→4) linkages. A portion (three monomeric units) of an α(1→4) glucopyranose polymer is shown below:

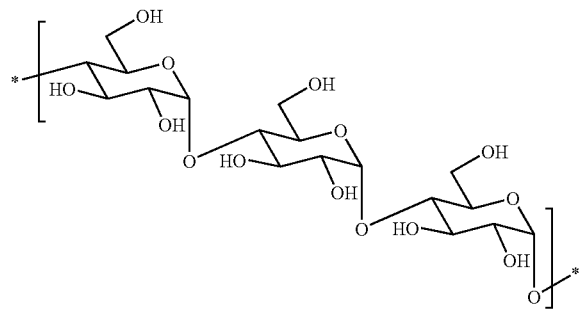

In many aspects the α(1→4)glucopyranose polymer is linear (i.e., a polymer that is substantially or entirely non-branched), or non-cyclic. By comparison, a branched α(1→4)glucopyranose polymer is exemplified by starch, and a cyclic α(1→4) glucopyranose polymer is exemplified by cyclodextrin.

Exemplary linear α(1→4)glucopyranose polymers are exemplified by maltodextrin and amylose.

"Amylose" or "amylose polymers" refers to linear polymers having repeating α-D-glucopyranose units that are joined by α-1,4 linkages. Some amylose polymers can have a very small amount of branching via α-1,6 linkages (about less than 0.5% of the linkages) but still demonstrate the same physical properties as linear (unbranched) amylose polymers do. Generally amylose polymers derived from plant sources have molecular weights of about $1 \times 10^6$ Da or less. Amylopectin, comparatively, is a branched polymer having repeating glucopyranose units that are joined by α-1,4 linkages to form linear portions and the linear portions are linked together via α-1,6 linkages. The branch point linkages are generally greater than 1% of the total linkages and typically 4%-5% of the total linkages. Generally amylopectin derived from plant sources have molecular weights of $1 \times 10^7$ Da or greater.

Amylose can be obtained from, or is present in, a variety of sources. Typically, amylose is obtained from non-animal sources, such as plant sources. Starch preparations having a high amylose content, purified amylose, synthetically prepared amylose, or enriched amylose preparations can be used for the preparation of amylose derivatives having pendent hydrazide or hydrazide-reactive groups.

Steps may be performed before, during, and/or after the process of derivatizing the amylose polymer to provide for a hydrophobic derivative, to enrich the amount of amylose, or to purify the amylose. For example, if an amount of amylopectin is present in a amylose preparation, the amount of amylopectin may be reduced by treating the starch with amylopectinase, which cleaves α-1,6 linkages resulting in the debranching of amylopectin into amylose.

Purified or enriched amylose preparations can be obtained commercially or can be prepared using standard biochemical techniques such as chromatography. For example, synthetic amyloses with an average molecular mass of 70 kDa can be obtained from Nakano Vinegar Co., Ltd. (Aichi, Japan).

As a general matter, "maltodextrins" refer to linear α(1→4)glucopyranose polymers, generally having a molecular weight that is, on average, less than amylose.

Maltodextrin is typically generated by hydrolyzing a starch slurry with heat-stable α-amylase at temperatures at 85-90° C. until the desired degree of hydrolysis is reached and then inactivating the α-amylase by a second heat treatment. The maltodextrin can be purified by filtration and then spray dried to a final product. Maltodextrins are typically characterized by their dextrose equivalent (DE) value, which is related to the degree of hydrolysis defined as: DE=MW dextrose/number-averaged MW starch hydrolysate X 100. Generally, maltodextrins are considered to have molecular weights that are less than amylose molecules.

A starch preparation that has been totally hydrolyzed to dextrose (glucose) has a DE of 100, whereas starch has a DE of about zero. A DE of greater than 0 but less than 100 characterizes the mean-average molecular weight of a starch hydrolysate, and maltodextrins are considered to have a DE of less than 20. Maltodextrins of various molecular weights, for example, in the range of about 500 Da to $1 \times 10^6$ Da are commercially available (for example, from GPC, Muscatine, Iowa and Roquette from France).

Preparations including α(1→4)glucopyranose polymers, such as maltodextrin and amylose, can be subjected to fractionation. For example, maltodextrin or amylose preparations can be subjected to diafiltration using ultrafiltration membranes with differing pore sizes, which has been described in commonly assigned U.S. patent application Ser. No. 11/904,805, published as U.S. Publication No. 2008/0089923A1 (Apr. 17, 2008). As an example, use of one or more cassettes with molecular weight cut-off membranes in the range of about 1K to about 500 K can be used in a diafiltration process to provide polysaccharide preparations with average molecular weights of less than 500 K Da, such as in the range of about 100 K Da to about 500 K Da, in the range of about 30 K Da to about 100 K Da, or in the range of about 1 K Da to about 30 K Da.

Because of the advantages of using amylose and maltodextrin polymers, in some aspects the α(1→4)glucopyranose polymer preparation has an average molecular weight of 500,000 Da or less, 250,000 Da or less, 100,000 Da or less, or 50,000 Da or less. Exemplary size ranges for the α(1→4)glucopyranose polymer preparations are in the range of about 1000 Da to about 500,000 Da, about 100,000 Da to about 500,000 Da, about 1000 Da to about 50,000 Da, about 1000 Da to about 30,000 Da, about 1000 Da to about 25,000 Da, about 1000 Da to about 20,000 Da, about 1000 Da to about 15,000 Da, and about 1000 Da to about 10,000 Da.

As used herein, the "molecular weight" of the polymer refers to the "weight average molecular weight" or $M_w$. $M_w$ is an absolute method of measuring molecular weight and is particularly useful for measuring the molecular weight of a polymer (preparation), such as preparations of polysaccharides. Polymer preparations typically include polymers that individually have minor variations in molecular weight. Polymers are molecules that have a relatively high molecular weight and such minor variations within the polymer preparation do not affect the overall properties of the polymer preparation. The weight average molecular weight ($M_w$) can be defined by the following formula:

$$M_w = \frac{\sum_i N_i M_i^2}{\sum_i N_i M_i}$$

wherein N represents the number of moles of a polymer in the sample with a mass of M, and $\Sigma_i$ is the sum of all $N_i M_i$ (species) in a preparation. The $M_w$ can be measured using common techniques, such as light scattering or ultracentrifugation. Discussion of $M_w$ and other terms used to define the molecular weight of polymer preparations can be found in, for example, Allcock, H. R. and Lampe, F. W. (1990) *Contemporary Polymer Chemistry*; pg 271.

In many aspects the matrix is prepared using α(1→4)glucopyranose polymer including a pendent first reactive group that includes a hydrazide group, and another α(1→4)glucopyranose polymer that includes a second reactive group that is reactive with the hydrazide groups.

Optionally, and in other aspects of the invention, the matrix can be prepared using an α(1→4)glucopyranose polymer including a pendent first reactive group, and a second component that is different than the α(1→4)glucopyranose polymer. For example, the second component can be a polymeric bifunctional crosslinker having a group reactive with the first group of the α(1→4)glucopyranose polymer. As another option, the matrix can be prepared using more than one component that is different than the α(1→4)glucopyranose polymer.

In some aspects the second component is derived from a biocompatible polymer. For example, the second component can be formed from a biocompatible hydrophilic polymer. Exemplary biocompatible hydrophilic polymers that can be used to form a second component for matrix formation include poly(vinylpyrrolidone) (PVP), poly(ethylene oxide) (PEO), poly(ethyloxazoline), poly(propylene oxide) (PPO), poly(meth)acrylamide (PAA) and poly(meth)acrylic acid, poly(ethylene glycol) (PEG), PEG-PPO (copolymers of polyethylene glycol and polypropylene oxide), hydrophilic segmented urethanes, and polyvinyl alcohol.

In some embodiments, the second component is prepared from a hydroxy-functional compound. Typically, the hydroxy-functional compound has at least 2 hydroxyl groups, and more specifically about 2 to 4 hydroxyl groups per molecule. The hydroxyl groups are derivatized to provide either hydrazide-reactive groups, or hydrazide groups, and therefore provide a defined, limited number of reactive groups on the second component. Such a second component can provide advantages for the formation of a biodegradable matrix according to the invention.

In some embodiments a hydroxy-functional compound is derivatized to provide a second component that has two hydrazide-reactive groups. In some aspects, the hydroxy-functional compound has a molecular weight of about 10,000 Da or less.

The second component can be prepared from a low molecular weight polyol. For example, the second component can be formed from poly(ethylene glycol), tetraethylene glycol, triethylene glycol, trimethylolpropane ethoxylate, or pentaerythritol ethoxylate. In some embodiments, the second component is based on an ethylene glycol polymer or oligomer having the structure HO—(CH$_2$—CH$_2$—O)$_n$—H. Exemplary values of n ranges from about 3 to about 150 and the number average molecular weight ($M_n$) of the poly(ethylene glycol) ranges from about 100 Da to about 20,000 Da, more typically ranging from about 200 Da to about 3500 Da.

The second component can also be prepared from a polypeptide. As used herein, a polypeptide refers to an oligomer or polymer including two or more amino acid residues, and is intended to encompass compounds referred to in the art as proteins, polypeptides, oligopeptides, peptides, and the like.

In some aspects the second component is prepared from a polypeptide that is a matrix protein, or portion thereof. The matrix protein, or portion thereof, can be a cell attachment factor. Exemplary cell attachment factors include those selected from fibronectin, vitronectin, laminin A, laminin B1, laminin B2, collagen I, and thrombospondin. Exemplary active portions of cell attachment factors include polypeptides selected from RGDS (SEQ ID NO:10), LDV, REDV (SEQ ID NO:13), RGDV (SEQ ID NO:12), LRGDN (SEQ ID NO:5), IKVAV (SEQ ID NO:6), YIGSR (SEQ ID NO:1), PDSGR (SEQ ID NO:8), RNIAEIIKDA (SEQ ID NO:9), RGDT (SEQ ID NO:11), DGEA (SEQ ID NO:2), GTPGPQ-GIAGQRGVV (SEQ ID NO:3), RGD, VTXG (SEQ ID NO:4), and FYVVMWK (SEQ ID NO:7).

In some modes of practice, the second component is prepared from polypeptides having a molecular weight in the range of about 150 Da to about 10,000 Da, about 200 to about 5,000 Da, or about 250 Da to about 2,500 Da.

α(1→4)glucopyranose polymers having pendent reactive hydrazide, or pendent hydrazide-reactive groups, can be prepared using techniques described herein, as well as techniques known in the art. As shown according to the structure herein, in a natural state, an α(1→4)glucopyranose polymer has three hydroxyl groups per α-D-glucopyranose monomeric unit. At least one hydroxyl group, and more typically, a portion of the hydroxyl groups of an α(1→4)glucopyranose polymer are derivatized to provide pendent reactive hydrazides, or pendent hydrazide-reactive groups on the polymer. For example, an α(1→4)glucopyranose polymer can be derivatized to provide two or more pendent reactive hydrazide, or pendent hydrazide-reactive groups, which can be spaced randomly along the length of the polymer.

In one mode of practice, preparation of a hydrazide functional α(1→4) glucopyranose polymer can be carried out using a α(1→4) glucopyranose polymer derived from a natural source, an activating agent, and hydrazine or a hydrazide-containing compound.

For polymer derivation, the choice of the concentration of the polymeric material, activating agent, and hydrazine or a hydrazide-containing compound, solvent, and reaction conditions (e.g., time and temperature) can be chosen based on the desired level of derivation of the α(1→4) glucopyranose polymer and the nature of the pendent hydrazide group.

The α(1→4) glucopyranose polymer can be dissolved in a suitable solvent system, including a polar solvent, or combination of solvents. An exemplary solvent is dimethyl sulfoxide (DMSO). Additionally, or alternatively, solvents such as N,N-dimethylformamide (DMF), pyridine, 1-methyl-2-pyrrolidinone, water, and nitrobenzene can be used.

For the activation step, various activation agents may be used which produce activated poly α(1→4)glucopyranose intermediates that react well with amino groups of hydrazine or a hydrazine-containing compounds. One preferred activating agent is 1,1'-carbonyldiimidazole (CDI). Alternatively, hydroxyl groups of the poly α(1→4)glucopyranose can be activated by reaction with chloroformates such as 4-nitrophenyl chloroformate, pentafluorophenyl chloroformate, and succinimidyl chloroformate. The number of activated hydroxyl groups formed along the polymer will generally be controllable by the relative amount or quantity of activating reagent used and by the reaction conditions. In one mode of practice the activating agent is used in an amount of about 3.1 mmol per gram of α(1→4)glucopyranose polymer. In some cases, synthesis can be carried out using an amount of activating agent to α(1→4)glucopyranose polymer in the range of about 0.1 mmol per gram to about 6 mmol per gram.

Hydrazine or a hydrazide group-containing compound can then be added to the solution containing the activated α(1→4) glucopyranose polymer. Typically, the hydrazine or hydrazide-containing compound is added in a molar excess over the amount of the activation agent added (e.g., a ten fold molar excess, or about a twenty fold molar excess). Hydrazine and a hydrazide group-containing compound of formula (a) are shown below:

$$H_2N-NH_2$$
(hydrazine)

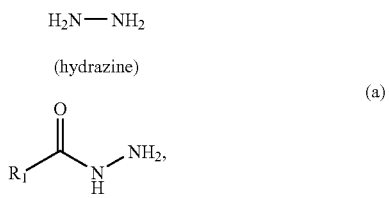

(a)

wherein $R_1$ of the hydrazide group-containing compound includes a group that is reactive with the activated hydroxyl groups of α(1→4)glucopyranose polymer.

One subset of hydrazide group-containing compounds is dihydrazide compounds. One particular dihydrazide compound is carbohydrazide, which can be used to create a hydrazide functional α(1→4) glucopyranose polymer.

One subset of hydrazide group-containing compounds are dihydrazide compounds of formula (b) as shown below:

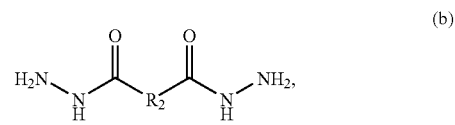

(b)

wherein $R_2$ is a covalent bond, a cyclic, linear, or branched carbon-containing group, such as one having 1-12 carbon atoms. In some aspects $R_2$ a $-(CH_2)_n-$ group, wherein n is from 1-12. Specific examples of dihydrazide compounds of formula (b) include oxalyldihydrazide, succinic dihydrazide, and adipic dihydrazide.

Other dihydrazide compounds of formula (b) are where $R_2$ includes a natural or synthetic amino acid residue.

In some aspects, $R_1$ of the hydrazide group-containing compound (a) includes a carboxyl, carboxylate, or ester group, which provides a compound of formula (c):

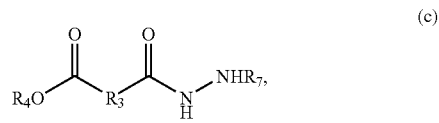

(c)

wherein $R_3$ is a cyclic, linear, or branched carbon-containing group; $R_4$ is H, or a cation; and $R_7$ is H or a protecting group.

In formula (c) $R_3$ can bridge the hydrazide group with the carboxyl, carboxylate, or ester group. In some aspects $R_3$ is a $-(CH_2)_n-$ group, wherein n is from 1-12. In some aspects $R_7$ is an acid sensitive protecting group. Exemplary acid sensitive protecting groups can be selected from the group consisting of t-butoxycarbonyl (BOC), trityl (trt), t-butyl dimethylsilyl (TBDMS), and carbobenzyloxy (Cbz) groups.

Exemplary hydrazide derivatives, for example maltodextrin-hydrazide (MD-Hyd) have a ratio of pendent hydrazide groups to maltodextrin in the range of about 0.1 mmol (Hyd) per gram (MD) to about 2 mmol (Hyd) per gram (MD), and more specifically in the range of about 0.5 mmol per gram to about 1.5 mmol per gram. One exemplary ratio is about 1.25 mmol per gram.

Another way of expressing levels of derivation is by degree of substitution (DS). For maltodextrin and other polysaccharides that have three hydroxyl groups per monomeric unit, substitution of one hydroxyl group (with a hydrazide-containing moiety) per monomeric unit, on average, is referred to a degree of substitution of 1 (DS 1), and a fully substituted maltodextrin has a DS of 3. Exemplary hydrazide derivatives, for example maltodextrin-hydrazide (MD-Hyd) have a DS in the range of about 0.05 to about 1.0, about 0.1 to about 1.0, and more specifically in the range of about 0.2 to about 0.7. One exemplary DS is about 0.5.

Examples of hydrazide-derivatized α(1→4)glucopyranose polymers are those that include one of the structures (d)-(g) shown below, wherein the meanings of $R_2$ and $R_3$ correspond to formulas (b) and (c) respectively.

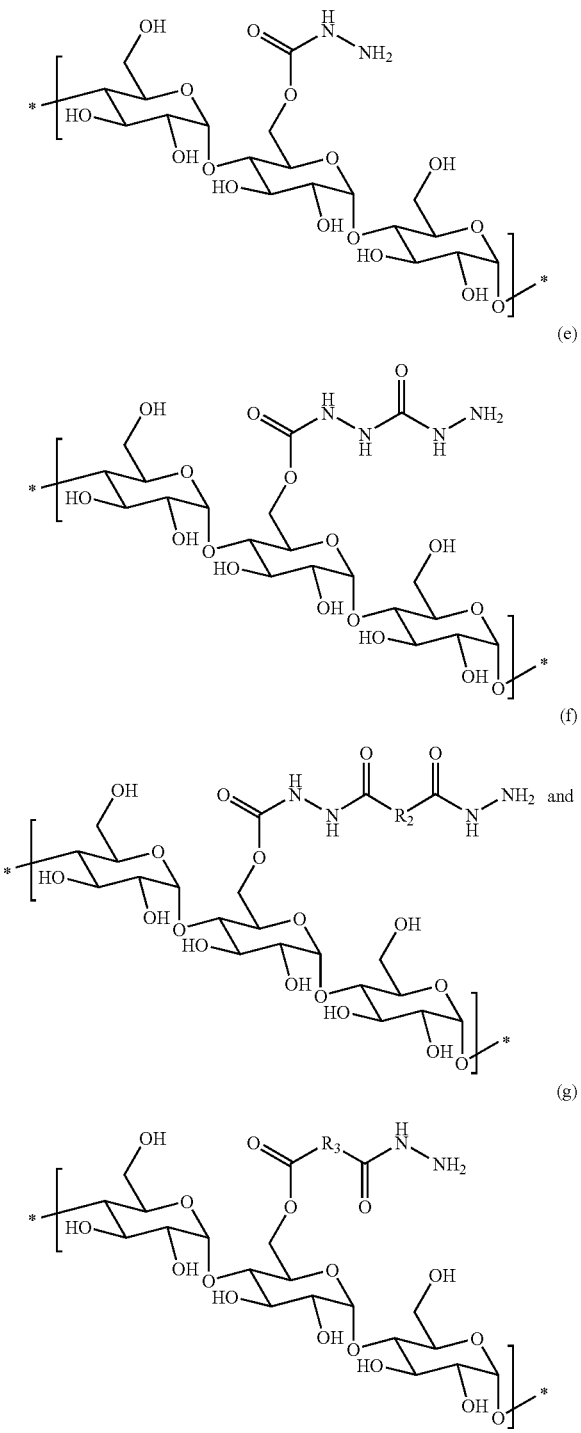

As a general matter, a polysaccharide with a higher degree of hydrazide substitution is more highly reactive with the second component. As a result, upon combination of the reactive components, compositions having more highly substituted polysaccharides gel rapidly, and result more highly crosslinked, firmer gels.

Preparation of α(1→4) glucopyranose polymers that have groups that are reactive with hydrazide groups, such as aldehyde groups, can be performed. In one mode of practice, preparation of an aldehyde-functional α(1→4) glucopyranose polymer can be carried out using an α(1→4) glucopyranose polymer and oxidizing agent.

An oxidizing agent, such an alkali metal periodate, can be used to convert hydroxyl groups of the glucopyranose ring to aldehyde groups. One known method involves using sodium periodate (NaIO$_4$), which can be performed under conditions to convert a limited number of hydroxyl groups of the glucopyranose ring to aldehyde groups. For example, the C$_2$ and C$_3$ hydroxyl groups of glucopyranose ring can be converted to a dialdehyde in the presence of sodium periodate.

The oxidation reaction is typically performed at a lower pH, such as in the range of about 4 to about 5. The number of aldehyde groups formed along the polymer will generally be controlled by the relative amount of sodium periodate and the reaction conditions. In one mode of practice the sodium periodate is used in an amount of about 1.54 mmol per gram of α(1→4)glucopyranose polymer. In some cases, synthesis can be carried out using an amount of sodium periodate to α(1→4) glucopyranose polymer in the range of about 0.1 mmol per gram to about 4 mmol per gram.

Other oxidizing agents, such as Dess-Martin periodinane (DMP), or 2,2,6,6-tetramethylpiperidine-1-oxyl radical (TEMPO), can be used to selectively oxidize primary hydroxyl groups.

If a second component that is different than the derivatized α(1→4)glucopyranose polymer is used to form the matrix, it can be prepared using a synthetic scheme involving hydrazide chemistry.

For example, in some aspects, the second component is formed by reaction of a polyol having a defined, limited number of hydroxyl groups, with an activating agent and a hydrazide. For example, hydrazide-derivatized poly(ethylene glycol) can be prepared using a reaction scheme similar to that for the preparation of hydrazide-polysaccharide.

For a diol such as polyethylene glycol, derivation can be carried out using an activating agent, such as CDI, in at least a two-fold molar excess over the diol. In some modes of practice, the molar ratio of activating agent to diol is in the range of about 2:1 to about 4:1. Generally, the dihydrazide compound should be used in a molar excess (e.g., ten-fold excess) over the activating agent or diol in order to prevent polymerization of the diol.

In other aspects, the second component comprises a hydrazide-derivatized polypeptide. Preferably, the hydrazide-derivatized polypeptide comprises a desired sequence, such as an active domain of a cell attachment protein, flanked by amino acid residues or sequences that are coupled to hydrazide groups (i.e., the polypeptide has pendent, reactive hydrazide groups used for matrix formation). In this regard, the chemistry of the sequence containing the active domain of a cell attachment protein is not altered by the hydrazide derivation, and the sequence can therefore maintain is natural cell attachment functionality.

In one mode of practice, the hydrazide-derivatized polypeptide is prepared by first (a) obtaining a peptide having a desired sequence flanked by N-terminal and C-terminal amino acid residues or sequences, the N-terminal and C-terminal amino acid residues or sequences including cysteine residues, and then (b) reacting the sulfhydryl groups of the cysteine residues with a component comprising a sulfhydryl-reactive group and a hydrazide group. The reaction is desirably performed at a pH around or below neutral, limiting the reaction between the sulfhydryl and sulfhydryl-reactive groups.

A desired peptide with flanking cysteine residues or cysteine-residue containing sequences can be synthesized by SPPS (solid phase peptide synthesis) using any combination of amino-terminal protecting and side chain protecting chemistries known in the art. Exemplary and suitable SPPS use conventional base-removable, 9-fluorenyl-methyloxycarbonyl (Fmoc) chemistry for amino-terminal protection. See, for example, Carpin et al. (1972), J. Org. Chem. 37(22):3404-3409, or "Fmoc Solid Phase Peptide Synthesis," Chan, W. C. and White, P. D., Eds. (2000) Oxford University Press Oxford Eng. Exemplary and suitable SPPS can also use conventional acid-sensitive side chain protecting groups (e.g., t-butoxycarbonyl (BOC), tert-butyl, t-butyl ester, etc.) appropriate for individual amino acids. Cleavage of the peptide from a resin, and side-chain protecting group removal can be carried out using known procedures, such as by acidolytic (e.g., using trifluoroacetic acid (TFA)) cleavage and global deprotection. If desired, the peptide can be purified using chromatographic, or other known suitable techniques.

SPPS can provide a peptide of the general formula $(NH_2)$—U—X—Z—(COOH), wherein U is an amino acid sequence including a cysteine residue, X is a desired amino acid sequence, such as an active domain of a cell attachment protein, and Z is another amino acid sequence including a cysteine residue. In exemplary embodiments, a peptide according to the formula U—X—Z is prepared, and has about 5 to about 20 amino acid residues, or about 5 to about 15 amino acid residues.

The deprotected and isolated peptide can then be reacted with a component having a sulfhydryl-reactive group and a hydrazide group to provide a peptide with hydrazide groups that are pendent from the cysteine residues of the peptide. Exemplary sulfhydryl reactive, hydrazide components include 3,3'-N-[ε-maleimidocaproic acid] hydrazide (EMCH), and the like, which can be obtained from Thermo Fisher Scientific Inc (Rockford, Ill.). The reaction can be performed in aqueous buffer, such as acetate, at a pH at or preferably below neutral, such as in the range of about 2 to about 7.5.

Preparation of a second component that has groups that are reactive with hydrazide groups, such as aldehyde groups, can be performed. For example, a hydroxyl-group containing compound such as a diol, can be reacted with an oxidizing agent, such as a periodate, to provide pendent reactive aldehyde groups.

Aldehyde-functionalized amino acids and peptides can also be obtained or synthesized. For example, diamino acids can be purchased or synthesized containing amino acids that have hydroxyl groups. Subsequently, the hydroxyl groups can be oxidized using TEMPO-mediated chemistry (or other oxidative chemistries known in the art) to create aldehyde groups. These reactive groups can then be crosslinked to a hydrazide component to make a biodegradable matrix.

The matrices of the invention can be prepared by combining an $\alpha(1\rightarrow 4)$ glucopyranose polymer including a pendent first reactive group, with a second component that includes second reactive groups that are reactive with the first reactive groups. Since the components are reactive with one another, they are generally kept separated until combined.

In many aspects, individual compositions (e.g., liquid composition) are prepared having the reactive matrix-forming components, and then the compositions are mixed to initiate gel formation. In some aspects, two compositions (e.g., compositions A and B, each having matrix forming components) are mixed together to form a mixed composition having the matrix-forming materials of at least an $\alpha(1\rightarrow 4)$ glucopyranose polymer with pendent first reactive groups, and another component which can be the same as, or different than the $\alpha(1\rightarrow 4)$ glucopyranose polymer, the second component having second groups which are reactive with the first groups.

Depending on the particular application, the mixed composition can have a certain amount of matrix-forming material. For the preparation of matrices capable of releasing bioactive agent by enzymatic degradation, it can be desirable to prepare the matrix using a mixed composition having a higher concentration of matrix forming material. In some aspects, the bioactive agent is a macromolecular agent, such as one selected from polynucleotides, polysaccharides, and polypeptides.

For example, for these matrices, the concentration of matrix-forming material in the mixture can be generally greater than about 20 mg/mL, about 25 mg/mL or greater, about 40 mg/mL or greater, about 50 mg/mL or greater, about 60 mg/mL or greater, about 70 mg/mL or greater, about 80 mg/mL or greater, about 90 mg/mL or greater, or about 100 mg/mL or greater, such as in the range of about 20 mg/mL to about 500 mg/mL, about 25 mg/mL (2.44% wt. solids) to about 250 mg/mL (20% wt. solids), about 40 mg/mL (3.85% wt. solids) to about 200 mg/mL (16.7% wt. solids), or about 50 (4.76% wt. solids) mg/mL to about 150 mg/mL (13% wt. solids). These concentrations can also be used when the matrix is formed in the presence of cells to provide cell scaffolding.

In some embodiments, the primary matrix-forming material in the mixture is derived from an $\alpha(1\rightarrow 4)$ glucopyranose polymer. That is, as the primary matrix forming component, the $\alpha(1\rightarrow 4)$ glucopyranose polymer derivatives are present in the mixture in an amount more than the amount of other matrix forming materials. In some cases the $\alpha(1\rightarrow 4)$ glucopyranose polymer derivatives are present in an amount of about 50% or greater (based on weight of solid matrix-forming materials), about 60% or greater, about 70% or greater, about 80% or greater, or about 90% or greater, of the total amount of matrix forming materials in the mixture. Exemplary ranges are from about 50% to about 99% (based on weight of solid matrix-forming materials), from about 60% to about 99%, from about 70% to about 99%, from about 80% to about 99%, or from about 90% to about 99%. In some aspect, the mixture contains no other, or insubstantial amounts of matrix forming material that is different than the $\alpha(1\rightarrow 4)$ glucopyranose derivative. In these aspects, substantially all of, or entirely all of the matrix-forming material in the mixture is derived from $\alpha(1\rightarrow 4)$ glucopyranose polymer.

In some embodiments, the mixture includes a second component that is a matrix-forming material that is different than one derived from an $\alpha(1\rightarrow 4)$ glucopyranose polymer (such as a hydrazide or hydrazide-reactive derivative of a diol compound), and the second component is present in an amount of less than about 50% (based on weight of solid matrix-forming materials), less than about 40%, less than about 30%, less than about 20%, or less than about 10% of the total amount of matrix forming materials in the mixture. Exemplary ranges are from about 1% to about 50% (based on weight of solid matrix-forming materials), from about 1% to about 40%, from about 1% to about 30%, from about 1% to about 20%, or from about 1% to about 10%. In exemplary embodiments, the second component is derived from poly(ethylene glycol) or a polypeptide.

The compositions that include the matrix forming material can also optionally include one or more other non-matrix forming materials, such as buffers, excipients, and/or bioactive agents.

The pH of the compositions can be controlled using conventional buffering materials such as phosphate, borate, and bicarbonate buffers. In most embodiments, the pH of the matrix-forming composition is between about 7 to about 8, which is beneficial for use with many sensitive bioactive agents, although other pH values may be suitable for certain applications.

Other polymers or non-polymeric compounds can be included in the mixture that can change or improve the properties of the matrix. These optional compounds can change the elasticity, flexibility, wettability, or adherent properties, (or combinations thereof) of the formed matrices.

Exemplary optional components include one or more plasticizing agents. Suitable plasticizing agents include glycerol, diethylene glycol, sorbitol, sorbitol esters, maltitol, sucrose, fructose, invert sugars, corn syrup, and mixtures thereof. The amount and type of plasticizing agents can be readily determined using known standards and techniques.

In some aspects of the invention, a functional agent is covalently attached to the polymeric materials forming the biodegradable matrix through a photoreactive group. The functional agent can be a macromolecular agent, such as one selected from polynucleotides, polysaccharides, and polypeptides. The functional agent can alter the properties of the matrix suitable for a desired application. For example, the matrix can be modified with a polypeptide that is a cell attachment factor; the polypeptide is then attached to the matrix material via a reacted photogroup. Such a modified matrix can provide improved conditions for cells if included in the matrix. Another example includes the attachment of a growth factor to the matrix, such as IGF to increase cell survival.

Biocompatible reagents, such a polynucleotides, polysaccharides, and polypeptides can be derivatized with latent reactive groups, such as latent photoreactive groups, which have been described in the art. Photoderivatized polypeptides, such as collagen, fibronectin, and laminin can be prepared as described in U.S. Pat. No. 5,744,515; photo-RGD can be prepared as described in U.S. Pat. No. 6,121,027. Latent photoreactive groups are those that respond to specific applied external stimuli to undergo active specie generation with resultant covalent bonding to a target. Latent reactive groups retain their covalent bonds unchanged under conditions of storage but which, upon activation, form covalent bonds with other molecules.

Photoderivation of matrix materials can be carried out using various methods. In one mode of practice, the photoreagent is mixed with a matrix-forming material, such as maltodextrin-hydrazide, and then activated to covalently bond the photo-reagent to the maltodextin-hydrazide. The hydrazide group remains unreacted, and the derivatized maltodextrin can then be combined with another matrix-forming material to form a gel. In another mode of practice, the photo-reagent is present when the matrix-forming materials are combined, and then activated after formation of the matrix to bond the reagent to the matrix materials. In yet another mode of practice, a matrix is formed in the absence of the photo-reagent, and then the photo-reagent is added to the formed matrix and activated to bond the reagent to the matrix material. Depending on the properties of the matrix (i.e., whether the matrix is permeable to the photo-reagent) the reagent can be bonded to the outside of the gel, or both on the outside and within the gel.

In some modes of practice, a photo-reagent, such as a photo-protein, is reacted with the matrix material in an amount in the range of about 1 ng to about 100 μg per 1 mg of matrix-forming material.

In some aspects of the invention, the matrix includes one or more bioactive agents. The compositions used to prepare the matrix can include a bioactive agent, which can become entrapped in the matrix when the matrix-forming materials are combined and the mixed composition gels.

A partial list of bioactive agents is provided below. A comprehensive listing of bioactive agents, in addition to information of the water solubility of the bioactive agents, can be found in The Merck Index, Thirteenth Edition, Merck & Co. (2001).

The matrices prepared according to the invention can be used to release bioactive agents falling within one or more of the following classes. These classes include, but are not limited to: ACE inhibitors, actin inhibitors, analgesics, anesthetics, anti-hypertensives, anti polymerases, antisecretory agents, anti-AIDS substances, anti-apoptotic, antibiotics, anti-cancer substances, anti-cholinergics, anti-coagulants, anti-convulsants, anti-depressants, anti-emetics, antifungals, anti-glaucoma solutes, antihistamines, antihypertensive agents, anti-inflammatory agents (such as NSAIDs), anti metabolites, antimitotics, antioxidizing agents, anti-parasite and/or anti-Parkinson substances, antiproliferatives (including antiangiogenesis agents), anti-protozoal solutes, antipsychotic substances, anti-pyretics, antiseptics, anti-spasmodics, antiviral agents, calcium channel blockers, cell cycle proteins, cell response modifiers, chelators, chemotherapeutic agents, dopamine agonists, extracellular matrix components, fibrinolytic agents, free radical scavengers, growth factors, growth hormone antagonists, homing factors, hypnotics, immunosuppressive agents, immunotoxins, inhibitors of surface glycoprotein receptors, microtubule inhibitors, miotics, muscle contractants, muscle relaxants, neurotoxins, neurotransmitters, polynucleotides and derivatives thereof, opioids, photodynamic therapy agents, prostaglandins, remodeling inhibitors, statins, steroids, thrombolytic agents, tranquilizers, vasodilators, and vasospasm inhibitors.

In some aspects of the invention, the matrix includes a bioactive agent that is a macromolecule. Exemplary macromolecules can be selected from the group consisting of polynucleotides, polysaccharides, and polypeptides. In some aspects the bioactive agent has a molecular weight of about 1000 Da or greater.

One class of bioactive agents that can be released from the matrix includes polynucleotides. As used herein "polynucleotides" includes polymers of two or more monomeric nucleotides. Nucleotides can be selected from naturally occurring nucleotides as found in DNA (adenine, thymine, guanine, and cytosine-based deoxyribonucleotides) and RNA (adenine, uracil, guanine, and cytosine-based ribonucleotides), as well as non-natural or synthetic nucleotides.

Types of polynucleotides that can be released from the matrix include plasmids, phages, cosmids, episomes, integratable DNA fragments, antisense oligonucleotides, antisense DNA and RNA, aptamers, modified DNA and RNA, iRNA (immune ribonucleic acid), ribozymes, siRNA (small interfering RNA), miRNA (micro RNA), locked nucleic acids and shRNA (short hairpin RNA).

Aptamers include DNA or RNA molecules and function similar to antibodies in that they are able to selectively bind to a target molecule, such as other nucleic acids and proteins. An example of a therapeutic aptamer is the pegylated anti-VEGF polynucleotide pegaptanib (Macugen™) for the treatment of age-related macular degeneration.

Antisense oligonucleotides hybridize to a specific complementary portion of a mRNA. Hybridization with the antisense molecule results in the degradation of the RNA duplex by RNAse H and in decreased production of the protein encoded by the targeted mRNA. Examples of antisense oligonucleotides approved for treatment of disease or undergoing clinical investigations include fomivirsen (CMV retinitis), alicaforsen (Crohn's disease), and oblimersen (cancer).

RNA interference (RNAi) refers to target-specific gene silencing, and can be performed using via short interfering RNA (siRNA). Double-stranded siRNA introduced into a cell is recognized by the RNA induced silencing complex, which separates the strands, promotes hybridization of the antisense strand to the target mRNA, and then cleaves the target strand. Accordingly, siRNAs can reduce expression of select proteins.

Some enzymatic RNA molecules, known as ribozymes, can catalyze the cleavage and destruction of target RNA molecules. A ribozyme known as Angiozyme™, which is specific for the mRNA of FLT-1, which encodes a VEGF receptors in angiogenesis, has been used to treat advanced solid tumors In some aspects, the matrix includes a polynucleotide having a size in the range of about 1000 bases to about 10,000 bases (plasmid DNA), or about 20 bases to about 1000 bases (single-stranded oligonucleotide), or about 19 bases to about 30 bases (siRNA).

The matrix can also include a carrier component to facilitate function of the nucleic acid. The carrier component can inhibit degradation and promote entry of the nucleic acid into a cell. Carrier components that can facilitate nucleic acid function include polycationic carrier components which can bind and condense nucleic acids and form complex structures with an excess positive charge.

Carrier components include, but are not limited to, cationic polymers and cationic lipids. Specific examples of carrier components include N-[1-(2,3-Dioleoyloxy)propyl]-N,N,N-trimethylammonium (DOTAP), polycation containing cyclodextrin, histones, cationized human serum albumin, aminopolysaccharides such as chitosan, peptides such as poly-L-lysine, poly-L-ornithine, and poly-4-hydroxy-L-proline ester, peptides including protein transduction domains, polyamines such as polyethylenimine (PEI), polypropylenimine, polyamidoamine dendrimers, and poly(beta-aminoesters). Other carrier agents can include solid nucleic acid lipid nanoparticles (SNALPs), liposomes, protein transduction domains and polyvinyl pyrrolidone (PVP). Additionally, carriers may also be conjugated to molecules which allow them to target specific cell types. Examples of targeting agents include antibodies and peptides which recognize and bind to specific cell surface molecules.

Carrier components are commercially available or can be prepared using techniques known in the art.

As an example, polycationic carriers can be included in the matrix at a weight ratio of nucleic acid to polycationic carrier in the range of about 10:1 to about 1:20.

Biodegradable matrices for the delivery of polynucleotides, particularly siRNA and plasmids, can be prepared with minimal degradation of the polynucleotide during their preparation. Also, when placed in vivo, the matrices can prevent degradation of polynucleotide within the matrix, and can also regulate its release over therapeutically effective periods of time.

The biodegradable matrices can also provide polynucleotide delivery using bio-particles, such as viral particles. Viral gene delivery is another therapeutic approach contemplated for the treatment of a subject, wherein the viral particles are released from the biodegradable matrices. Examples of viral systems that can be included in and released from the matrices are adenoviruses, adeno-associated viruses, retroviruses, lentiviruses, and others.

In aspects, the matrices include a polypeptide which can be released from the matrix. A polypeptide refers to an oligomer or polymer including two or more amino acid residues, and is intended to encompass compounds referred to in the art as proteins, polypeptides, oligopeptides, peptides, and the like. By way of example, peptides can include antibodies (both monoclonal and polyclonal), antibody derivatives (including diabodies, F(ab) fragments, humanized antibodies, etc.), cytokines, growth factors, receptor ligands, enzymes, and the like. Polypeptides also include those modified with, or conjugated to, another biomolecule or biocompatible compound. For example, the polypeptide can be a peptide-nucleic acid (PNA) conjugate, polysaccharide-peptide conjugates (e.g., glycosylated polypeptides and glycoproteins), or a poly(ethyleneglycol)-polypeptide conjugate (PEG-ylated polypeptides).

One class of polypeptides that can be included in the matrix is antibodies and antibody fragments. A variety of antibody and antibody fragments are commercially available, obtainable by deposit or deposited samples, or can be prepared by techniques known in the art. For example, monoclonal antibodies (mAbs) can be obtained by any technique that provides for the production of antibody molecules by continuous cell lines in culture. These include, for example, the hybridoma technique (Kohler and Milstein, Nature, 256:495-497 (1975)); the human B-cell hybridoma technique (Kosbor et al., Immunology Today, 4:72 (1983); and the EBV-hybridoma technique (Cole et al., Monoclonal Antibodies and Cancer Therapy, Alan R. Liss, Inc., pp. 77-96 (1985)). Such antibodies may be of any immunoglobulin class including IgG, IgM, IgE, IgA, IgD and any subclass thereof.

Fab or Fab'2 fragments can be generated from monoclonal antibodies by standard techniques involving papain or pepsin digestion, respectively. Kits for the generation of Fab or Fab'2 fragments are commercially available from, for example, Pierce Chemical (Rockford, Ill.).

Examples of antibodies and antibody fragments include, but are not limited to, therapeutic antibodies include trastuzumab (Herceptin™), a humanized anti-HER2 monoclonal antibody (mAb); alemtuzumab (Campath™), a humanized anti-CD52 mAb; gemtuzumab (Mylotarg™), a humanized anti-CD33 mAb; rituximab (Rituxan™), a chimeric anti-CD20 mAb; ibritumomab (Zevalin™), a murine mAb conjugated to a beta-emitting radioisotope; tositumomab (Bexxar™), a murine anti-CD20 mAb; edrecolomab (Panorex™), a murine anti-epithelial cell adhesion molecule mAb; cetuximab (Erbitux™), a chimeric anti-EGFR mAb; bevacizumab (Avastin™), a humanized anti-VEGF mAb, Ranibizumab (Lucentis™), an anti-vascular endothelial growth factor mAb fragment, satumomab (OncoScint™) an anti-pancarcinoma antigen (Tag-72) mAb, pertuzumab (Omnitarg™) an anti-HER2 nAb, and daclizumab (Zenapax™) an anti IL-2 receptor mAb.

The polypeptide can also be selected from cell response modifiers. Cell response modifiers include chemotactic factors such as platelet-derived growth factor (PDGF), pigmented epithelium-derived factor (PEDF), neutrophil-activating protein, monocyte chemoattractant protein, macrophage-inflammatory protein, SIS (small inducible secreted) proteins, platelet factor, platelet basic protein, melanoma growth stimulating activity, epidermal growth factor, transforming growth factor (alpha), fibroblast growth factor, platelet-derived endothelial cell growth factor, insulin-like growth factor, nerve growth factor, vascular endothelial growth factor, bone morphogenic proteins, and bone growth/cartilage-inducing factor (alpha and beta). Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin.

The polypeptide can also be selected from therapeutic enzymes, such as proteases, phospholipases, lipases, glycosidases, cholesterol esterases, and nucleases.

Specific examples include recombinant human tissue plasminogen activator (alteplase), RNaseA, RNaseU, chondroitinase, pegaspargase, arginine deaminase, vibriolysin, sarcosidase, N-acetylgalactosamine-4-sulfatase, glucocerebrocidase, α-galactosidase, and laronidase.

In some aspects the matrix includes a bioactive agent, and the bioactive agent is present in a microparticle. The microparticles can be formed completely or substantially of a selected bioactive agent for treatment or prevention of a condition. Alternatively, the microparticles can be formed from a combination of bioactive agents (e.g., two or more different bioactive agents). In other cases, the microparticles can be formed from a bioactive agent and another component that is not intended to provide a therapeutic effect to the subject, such as a polymer that can further modulate the release of the bioactive agent from the microparticles (in addition to any release-modulating effect that the matrix provides).

The bioactive agent-containing microparticles can include one or more release control components to modulate release of the bioactive agent from the microparticle. In some aspects, the release control component is a material present in the microparticle that erodes, dissolves, and/or degrades after the microparticles are in contact with body fluid or tissue. The erosion, dissolution, or degradation of one or more components can slow the release of bioactive agent from the microparticle so the bioactive agent is present in more therapeutically effective amounts over a desired period of treatment. In some aspects, the microparticles comprises a bioactive agent and one or more degradable or erodable polymers.

Alternatively, the matrix can include microparticles that are formed substantially or entirely of a bioactive agent. Microparticles formed solely of one or more bioactive agents have been described in the art. For example, the preparation of paclitaxel microparticles has been described in U.S. Pat. No. 6,610,317. Therefore, in some aspects of the invention, the microparticles are composed of a low molecular weight bioactive agent.

In some preparations, the matrix comprises microparticles composed predominantly of polypeptides. Polypeptide microparticles can be formed as described in commonly owned U.S. patent application Ser. No. 12/215,504, published as US20090028956 (Slager et al.), and entitled "Polypeptide Microparticles." Generally, these microparticles are formed in a solution, by coalescing polypeptides with a nucleating agent to form polypeptide nuclei; mixing a phase separation agent with the solution to further coalesce polypeptide around the polypeptide nuclei, thereby forming a mixture; cooling the mixture to form polypeptide microparticles; and removing all or part of the phase separation agent from the polypeptide microparticles. This method is particularly advantageous for the preparation of microparticles formed predominantly of antibody or antibody fragments, and provides microparticle sets having microparticles of desired sizes, with low size polydispersity, and which maintains good polypeptide activity. Therefore, in another aspect of the invention, the microparticles are composed of higher molecular weight bioactive agents, such as polypeptides.

In another aspect, the matrix is in form of a cell scaffolding. As used herein, a "cell scaffolding" refers to a matrix of polymeric material including polymeric segments including poly-α(1→4)glucopyranose and linker segments as described herein, suitable for sustaining and delivering cells.

The cell scaffolding can be used in the body by itself, or in combination with an implantable article or device. Such examples include collagen sponges, vascular grafts, sensors, meshes, patches and the like.

The cell scaffolding can serve as an augmentation, repair, functional repair, and/or replacement tissue structure. Typically, the cell scaffolding will be formed or will be implanted and placed near, on, or in a tissue targeted for treatment to alter the normal wound healing response, which results in nonfunctional scar tissue. Following a period of implantation, the cell scaffolding will typically undergo degradation. Before, during, or after degradation of the cell-scaffolding matrix, the scaffolding will promote tissue repair.

For example, the scaffolding can promote remodeling of surrounding tissues within the mammalian host. Thus, in some aspects, the cell scaffolding can function to promote tissue replacement, and also function as a remodeling template for tissue repair.

Suitable cell scaffoldings can have properties suitable for repair and/or replacement of host tissues when implanted, including chemical, physical and/or structural properties. Illustrative chemical properties of the cell scaffoldings include chemistries that are suitable for cell attachment and growth when the scaffolding is implanted or formed within a subject. The cell scaffolding can include components such as cell attachment factors, growth factors, and/or cytokines, useful for maintaining the viability of the cells, and/or for promoting a cellular response that is a part of the tissue regeneration process. Illustrative physical properties include mechanical properties similar to those of the tissue at the site of implantation. For example, when the cell scaffolding is formed or implanted at a location on or within the heart (an organ that is constantly in motion), the cell scaffolding can be selected to possess mechanical properties that will allow it to move with the patient heart tissue while providing the structural integrity for the desired treatment. The scaffolding can also confer additional mechanical properties to increase the mechanical strength of the damaged tissue, thus reducing wall stress. The additional molecules could also help cells survive the often unfavorable and diseased areas where cellular therapy targets, and/or could help modulate the local microenvironment. As the matrix is degraded the cells have the potential to integrate or migrate into the local tissue and also remodel the degrading matrix to provide a greater clinical outcome.

The cell scaffoldings can have structural properties that allow cells to be viably maintained within the matrix. Cell attachment to the matrix materials can be facilitated using components and methods described herein, and proliferation of cells can also be promoted. The structural properties of the matrix can also allow components produced by the cells to diffuse out of the matrix, and nutrient components to diffuse in.

Regarding structural properties, the tissue scaffolding comprises an open pore network that is composed of a polymeric network formed of polymeric segments including the poly-α(1→4)glucopyranose and linker segments described herein. The cell scaffolding can be prepared to have a desirable mean pore size that is sufficient for allowing infusion of molecular components (such as polypeptides and lower molecular weight components) in and out of the scaffolding. Preparation of cell scaffolding matrices can be performed using the method and components described herein.

In some cases, the porosity of the matrix can be increased by including gas-generating components in the matrix-forming composition. These gas-generating components can effectively foam the matrix as it gels, creating micro-bubbles within the matrix. The gas-generating component includes two compounds that are separated into two compositions of the system. One compound is the gas-generating compound and the other is an activator that is reactive with the gas-generating compound to cause release of the gas. An exemplary pair representing the gas-generating component is a carbonate-containing compound, such as a bicarbonate salt (e.g., potassium or sodium bicarbonate) and a biocompatible acid, for example, citric acid, etc. Exemplary pore-forming compositions are described in commonly owned U.S. patent application Ser. No. 12/284,210, published as US20090093550 (Rolfes et al.)

Matrices with these larger pore sizes could effectively retain the cells within the matrix as long as the matrix is intact, but would allow certain components present in body fluids to diffuse into the matrix, as well as allowing components that are produced from the cell to diffuse out of the matrix and provide a biological effect to tissue in the vicinity of the matrix. Foamed matrices with large pore sizes allow cells to network and quickly deliver vascular supplies.

The cell scaffoldings can be prepared to provide a desirable degradation rate when formed or placed in vivo. Applicable rates can range from days to over 12 months. As the matrix is degraded at the target site in vivo, it can be replaced with regenerated tissues and cells. In some embodiments, the cell scaffoldings are prepared to maintain cells for a period of time on the order of hours to days to weeks, to months. As the scaffolding degrades, the entrapped cellular material continues to provide a regenerative effect to the local tissue. Over the course of degradation, the cells entrapped in the scaffolding may produce factors (e.g., growth factors) which increase the rate of endothelialization into the matrix.

Various types of cells can be included in the matrix, depending on the type of treatment that is carried out with the cell scaffolding of the present invention. Examples of cells that can be included in the matrix include platelets, differentiated and undifferentiated stem cells (adult and embryonic), including induced pluripotent stem cells, T lymphocytes, B lymphocytes, acidophils, adipocytes, astrocytes, basophils, hepatocytes, neurons, cardiac muscle cells, chondrocytes, epithelial cells, dendrites, endrocrine cells, endothelial cells, eosinophils, erythrocytes, fibroblasts, follicular cells, ganglion cells, hepatocytes, endothelial cells, Leydig cells, parenchymal cells, lymphocytes, lysozyme-secreting cells, macrophages, mast cells, megakaryocytes, melanocytes, monocytes, myoid cells, neck nerve cells, neutrophils, oligodendrocytes, oocytes, osteoblasts, osteochondroclasts, osteoclasts, osteocytes, plasma cells, spermatocytes, reticulocytes, Schwann cells, Sertoli cells, skeletal muscle cells, and smooth muscle cells. Cells that can be included in the matrix can also include genetically modified, recombinant, hybrid, mutated cells, and cells with other alterations.

In some aspects, the cell scaffoldings are formed using matrix-forming components that include a material that is different than the poly-$\alpha(1\rightarrow 4)$glucopyranose. In some aspects the second component includes a polypeptide that is functional as a cell attachment factor. For example, a cell scaffolding can be prepared by combining a poly-$\alpha(1\rightarrow 4)$ glucopyranose having pendent hydrazide groups, and a cell attachment peptide having pendent aldehyde groups in the presence of cells to be entrapped in the scaffolding. Upon its formation, the segments of the matrix that include the peptide serve as points within the matrix that the entrapped cells can attach to.

The presence of cell attachment segments within the matrix forming the cell scaffolding is desirable as it permits points on which the cells can attach. Many cells are anchorage dependent, meaning that they must demonstrate some type of attachment to a substrate in order to proliferate or differentiate. In vivo, cells can attach to protein factors present in the basement membrane, which is a structure that supports an overlying epithelium or endothelium. ECM proteins that promote cell attachment are commonly found in human tissue. The basement membrane consists of a membrane called the basal lamina and an underlying network of collagen fibrils.

Cell attachment factors can be introduced into the matrix in a variety of ways. One general method is to provide the cell attachment factor covalently attached to the matrix forming materials. In one mode of practice, a cell attachment factor is a protein or peptide that is covalently linked to the of a $\alpha(1\rightarrow 4)$ glucopyranose polymer via the linker segments. For example, a peptide including reactive aldehyde groups can be reacted with pendent hydrazide groups of the $\alpha(1\rightarrow 4)$ glucopyranose polymer. In another mode of practice, a cell attachment factor is a protein or peptide that includes a photoreactive group that is reacted to covalently link it to a portion of the matrix forming material.

Other factors can be included in the matrix, such as to maintain cell viability and inhibit apoptosis, to cause production of a biological factor from the cells to promote differentiation, or to promote growth or proliferation of the cells.

In some cases a growth factor and/or a differentiation factor is associated with the matrix. One or more growth or differentiation factors can be included in a matrix-forming composition which includes cells and the matrix-forming components. The matrix can be formed without covalently bonding the growth or differentiation factor to a the matrix forming material.

The term "growth factor" as used herein means a bioactive molecule that promotes the proliferation of a cell or tissue. Exemplary growth factors include, but are not limited to, transforming growth factor-alpha. (TGF-$\alpha$), transforming growth factor-beta. (TGF-$\beta$), platelet-derived growth factors including the AA, AB and BB isoforms (PDGF), fibroblast growth factors (FGF), including FGF acidic isoforms 1 and 2, FGF basic form 2, and FGF 4, 8, 9 and 10, nerve growth factors (NGF) including NGF 2.5s, NGF 7.0s and beta NGF and neurotrophins, brain derived neurotrophic factor, cartilage derived factor, bone growth factors (BGF), basic fibroblast growth factor, insulin-like growth factor (IGF), vascular endothelial growth factor (VEGF), EG-VEGF, VEGF-related protein, Bv8, VEGF-E, granulocyte colony stimulating factor (G-CSF), insulin like growth factor (IGF) I and II, hepatocyte growth factor, glial neurotrophic growth factor (GDNF), stem cell factor (SCF), keratinocyte growth factor (KGF), transforming growth factors (TGF), including TGFs alpha, beta, beta1, beta2, and beta3, skeletal growth factor, bone matrix derived growth factors, and bone derived growth factors and mixtures thereof. Some growth factors may also promote differentiation of a cell or tissue. TGF, for example, may promote growth and/or differentiation of a cell or tissue. Some preferred growth factors include VEGF, NGFs, PDGF-AA, PDGF-BB, PDGF-AB, FGFb, FGFa, and BGF.

The term "differentiation factor" as used herein means a bioactive molecule that promotes the differentiation of cells. The term includes, but is not limited to, bone morphogenic proteins (BMP), neurotrophin, colony stimulating factor (CSF), or transforming growth factor. CSF includes granulocyte-CSF, macrophage-CSF, granulocyte-macrophage-CSF, erythropoietin, and IL-3. Some differentiation factors may also promote the growth of a cell or tissue. TGF and IL-3, for example, may promote differentiation and/or growth of cells.

Growth factors or differentiation factors can be present in a microparticle, such as one described in US20090028956, supra.

In order to form the biodegradable matrix, generally, the first and second matrix-forming components are maintained apart from one another until matrix formation is desired. Matrix formation can occur by simply mixing the matrix-forming components and allowing gel formation to occur.

In one mode of preparing the matrix, the first and second matrix-forming components are held in separate chambers of dual syringe mixing device. When matrix formation is desired, simultaneous application of hand pressure to both syringe plungers in the device causes both the first and second component to flow from their respective syringes into a stationary mixing device (e.g., a "split flow" type mixer) where the first and second components are mixed with one another at a predetermined ratio. After being mixed, the mixed composition exits the device though a single outlet orifice which can be positioned at the desired application site. Useful dual syringe mixing devices are commercially available under the trade designation "MIXPAC" from Mixpac Systems AG (Rotkreuz, CH).

In some aspects, efficient mixing can be promoted by preparing compositions wherein the composition including the first component, and the composition including the second component have approximately the same viscosity. The viscosity may be controlled, for example, by adjusting the percent solids (% solids) of the components by appropriate dilution with the appropriate buffered solution including, but not limited to, phosphate buffered saline (PBS).

The matrix forming components of the invention can be reacted to provide a crosslinked matrix.

For example, in some aspects a portion of the matrix includes a chemical structure of following formula (h) or (i):

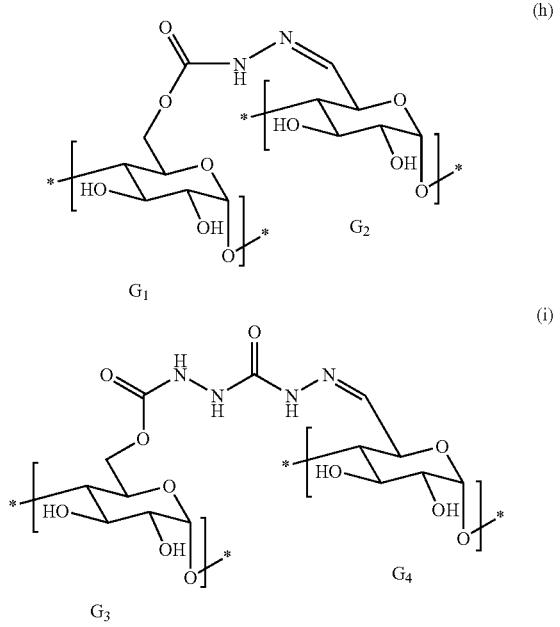

where $G_1$-$G_4$ in formulas (h) and (i) represent monomeric units of the poly-α(1→4)glucopyranose of the polymeric segments. In some embodiments, $G_1$ or $G_2$, is replaced with a chemical group from a polymer that is different than the α(1→4)glucopyranose polymer (for example, a group from a polymeric polyol, such as poly(ethylene glycol)). Likewise, in some embodiments, $G_3$ or $G_4$, is replaced with a chemical group from a polymer that is different than the α(1→4)glucopyranose polymer.

In some aspects, a portion of the matrix (primarily showing the linker segment) includes a chemical structure of one of the following formulas (j) or (k):

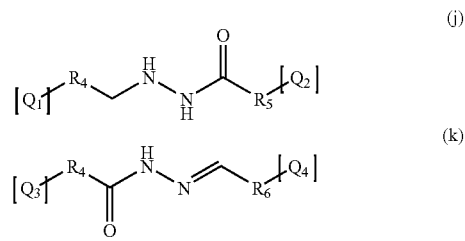

where, in structure (j), $Q_1$ and $Q_2$ represent monomeric units α(1→4) glucopyranose polymers, or one of $Q_1$ or $Q_2$ represent a portion of a polymeric component that is different than a α(1→4) glucopyranose polymer, provided that at least one of $Q_1$ or $Q_2$ is a monomeric unit of an α(1→4) glucopyranose polymer; and $R_4$ and $R_5$ are, independently O, or a cyclic, linear, or branched carbon-containing groups that contain one or more heteroatoms such as oxygen and/or nitrogen.

In structure (k), $Q_3$ and $Q_4$ represent monomeric units of α(1→4) glucopyranose polymers, or one of $Q_3$ or $Q_4$ represent a portion of a polymeric component that is different than the α(1→4) glucopyranose polymer, provided that at least one of $Q_3$ or $Q_4$ is a monomeric unit of a α(1→4) glucopyranose polymer and $R_6$ is a covalent bond, or a cyclic, linear, or branched carbon-containing groups that contain one or more heteroatoms such as oxygen and/or nitrogen.

In some aspects, the linker group includes an ester group. For example, in some aspects a portion of the matrix (primarily showing the linker segment) includes a chemical structure of one of the following formulas (l) or (m):

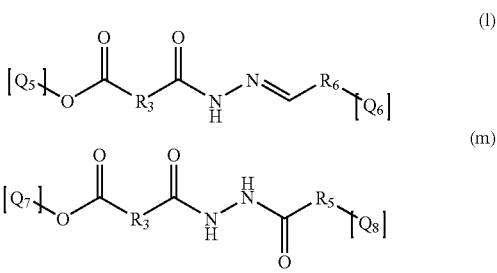

In structure (l), $Q_5$ and $Q_6$ represent monomeric units of α(1→4) glucopyranose polymers, or one of $Q_5$ or $Q_6$ represent a portion of a polymeric component that is different than the α(1→4) glucopyranose polymer, provided that at least one of $Q_5$ or $Q_6$ is a monomeric unit of a α(1→4) glucopyranose polymer; $R_3$ is a cyclic, linear, or branched carbon-containing group; and $R_6$ is a covalent bond, or a cyclic, linear, or branched carbon-containing groups that contain one or more heteroatoms such as oxygen and/or nitrogen. In some aspects $R_3$ is a —$(CH_2)_n$— group, wherein n is from 1-12.

In structure (m), $Q_7$ and $Q_8$ represent monomeric units of $\alpha(1\rightarrow4)$ glucopyranose polymers, or one of $Q_7$ or $Q_8$ represent a portion of a polymeric component that is different than the $\alpha(1\rightarrow4)$ glucopyranose polymer, provided that at least one of $Q_7$ or $Q_8$ is a monomeric unit of a $\alpha(1\rightarrow4)$ glucopyranose polymer; $R_3$ is a cyclic, linear, or branched carbon-containing group; and $R_5$ is O, or a cyclic, linear, or branched carbon-containing groups that contain one or more heteroatoms such as oxygen and/or nitrogen.

In some aspects $R_3$, in either structure (l) or (m), is a $-(CH_2)_n-$ group, wherein n is from 1-12.

For example, in some cases, the linker segments of the matrix include a chemical group formed by the reaction of a hydrazide group with a group selected from aldehyde, acyl halide, NHS-ester, carboxylic acid, imido-ester, hydroxyl methyl phosphine, and unsaturated ester. In specific aspects the linker segments of the matrix include a chemical group formed by the reaction of a hydrazide group with an aldehyde group.

Testing can be carried out to determine mechanical properties of the formed matrix. Dynamic mechanical thermal testing can provide information on the viscoelastic and rheological properties of the matrix by measuring its mechanical response as it is deformed under stress. Measurements can include determinations of compressive modulus, and shear modulus. Key viscoelastic parameters (including compressive modulus and sheer modulus) can be measured in oscillation as a function of stress, strain, frequency, temperature, or time. Commercially available rheometers (for example, available from (TA Instruments, New Castle, Del.) can be used to make these measurements. The testing of hydrogels for mechanical properties is also described in Anseth et al. (1996) *Mechanical properties of hydrogels and their experimental determination*, Biomaterials, 17:1647.

The matrix can be measured to determine its complex dynamic modulus ($G^*$): $G^*=G'+iG''=\sigma^*/\gamma^*$, where G' is the real (elastic or storage) modulus, and G" is the imaginary (viscous or loss) modulus, these definitions are applicable to testing in the shear mode, where G refers to the shear modulus, σ to the shear stress, and γ to the shear strain.

The matrix can also be measured for its swelling (or osmotic) pressure. Commercially available texture analyzers (for example, available from Stable Micro Systems; distributed by Texture Technologies Corp; Scarsdale, N.Y.) can be used to make these measurements. Texture analyzers can allow measurement of force and distance in tension or compression.

In some methods of use, matrix formation is carried out in situ, such as at a target tissue site wherein the matrix-forming components set up to form a gel. An in situ formed matrix can be used for the treatment of any one or more of a variety of medical conditions or indications, including restoring, improving, and/or augmenting tissue growth or function. Exemplary applications include those for the in situ treatment of cardiovascular, orthopedic, neuronal, diabetic, dental, spinal and bone graft problems. These functions can be provided by placing or forming a matrix of the biodegradable material of the invention in contact with a host tissue. The matrix can restore or improve tissue growth or function by, for example, promoting or permitting formation of new tissue between and/or into the matrix. The effect on tissue can be caused by the matrix material itself, bioactive agent released from the matrix (such as a bioactive agent produced from cells in a cell scaffolding), by cells, if present, or combinations thereof.

In some methods of use, the matrix is formed into an article, or is associated with a device, prior to introducing the matrix in the body. For example, the matrix can be in the form of an article having a defined structure, which can be implanted in the body (such as a filament or mesh). Such articles are referred to herein as "medical implants." A medical implant having a defined structure can be formed by any suitable process, including molding, extruding, shaping, cutting, casting, and the like. In one mode of practice, compositions including the reactive components are mixed and injected into a mold which forms matrix into an article of a desired shape.

The article can be used for one or more purposes, such as for releasing or retaining a bioactive agent at a location in the body. For example, the article can be a bioactive agent-containing medical implant or depot. The article can also provide one or more mechanical or physical properties to a portion the body. Biodegradable articles can degrade within a period that is acceptable for the desired application.

In some aspects the matrix is in the form of a coating. A "coating" as used herein can include one or more "coated layers", each coated layer including one or more coating materials. In many cases, the coating consists of a single layer of material that includes the polymeric materials forming the matrix. In other cases, the coating includes more than one coated layer, at least one of the coated layers including the polymeric materials forming the matrix. If more than one layer is present in the coating, the layers can be composed of the same or different materials.

The matrix forming materials can be applied to the surface of a device to form a coating in a variety of ways. For example, a coated layer can be formed by, for example, dipping, spraying, bushing, or swabbing the matrix-forming material on a surface of the device, and allowing the material to cure on the surface to form the coating. In some cases the reactive components can be mixed prior to application of the mixed composition to the surface of a device. In other cases the reactive components can be applied individually to the surface of the device, and when the components come in contact with each other, they cure to form the coating on the device.

In some cases, the matrix forming materials form a sealant on the surface of an implantable device. A sealant can provide a barrier on a surface that is impermeable to fluids within the body. Gradually, the sealant can degrade and its function can be replaced by tissue that infiltrates the material of the matrix. Therefore, the sealant coating has particular properties, such as biodegradability and relative impermeability (i.e., relative to the degradation of the sealant coating). The sealant coating can also be compliant and/or conformal, and can have properties such as flexibility, elasticity, and bendability.

As used herein, impermeable, used in relation to the function of the sealant coating, refers to a significant reduction in the transmission of bulk liquid or fluids through the substrate which the sealant coating is associated with. For example, the sealant coating can be impermeable to the transmission of blood. The impermeability can be maintained as the matrix degrades, and is replaced by tissue.

The matrix can be associated with the implantable device or article in any suitable manner or form, such as in the form of a coating, an overcoat, sealant, or a filler. The implantable device or article can be one that is introduced temporarily or permanently into a mammal for the prophylaxis or treatment of a medical condition. These devices include any that are introduced subcutaneously, percutaneously or surgically to rest within an organ, tissue, or lumen of an organ, such as arteries, veins, ventricles, or atria of the heart.

Exemplary medical articles include vascular implants, grafts, surgical devices; synthetic prostheses; vascular prosthesis including endoprosthesis, stent-graft, and endovascular-stent combinations; small diameter grafts, abdominal aortic aneurysm grafts; wound dressings and wound management device; hemostatic barriers; mesh and hernia plugs; patches, including uterine bleeding patches, atrial septic defect (ASD) patches, patent foramen ovale (PFO) patches, ventricular septal defect (VSD) patches, and other generic cardiac patches; ASD, PFO, and VSD closures; percutaneous closure devices, mitral valve repair devices; left atrial appendage filters; valve annuloplasty devices, catheters; central venous access catheters, vascular access catheters, abscess drainage catheters, drug infusion catheters, parenteral feeding catheters, intravenous catheters (e.g., treated with antithrombotic agents), stroke therapy catheters, blood pressure and stent graft catheters; anastomosis devices and anastomotic closures; aneurysm exclusion devices; biosensors including glucose sensors; cardiac sensors; birth control devices; breast implants; infection control devices; membranes; tissue scaffoldings; tissue-related materials; shunts including cerebral spinal fluid (CSF) shunts, glaucoma drain shunts; dental devices and dental implants; ear devices such as ear drainage tubes, tympanostomy vent tubes; ophthalmic devices; cuffs and cuff portions of devices including drainage tube cuffs, implanted drug infusion tube cuffs, catheter cuff, sewing cuff; spinal and neurological devices; nerve regeneration conduits; neurological catheters; neuropatches; orthopedic devices such as orthopedic joint implants, bone repair/augmentation devices, cartilage repair devices; urological devices and urethral devices such as urological implants, bladder devices, renal devices and hemodialysis devices, colostomy bag attachment devices; biliary drainage products.

In some aspects, the matrix is associated with an ophthalmic article. The ophthalmic article can be configured for placement at an external or internal site of the eye. In some aspects, the matrix associated with the article can be used to bioactive agent to an anterior segment of the eye (in front of the lens), and/or a posterior segment of the eye (behind the lens).

Articles configured for placement at an internal site of the eye can reside within any desired area of the eye. In some aspects, the ophthalmic article can be configured for placement at an intraocular site, such as the vitreous. Illustrative intraocular devices include, but are not limited to, those described in U.S. Pat. No. 6,719,750 B2, which describes a non-linear intraocular device. ("Devices for Intraocular Drug Delivery," Varner et al.) and U.S. Pat. No. 5,466,233 ("Tack for Intraocular Drug Delivery and Method for Inserting and Removing Same," Weiner et al.).

The matrices of the invention can be associated with implantable articles that have porous surfaces. In many cases the porous surface of the article is a fabric or has fabric-like qualities. The porous surface can be formed from textiles, which include woven materials, knitted materials, and braided materials. Particularly useful textile materials are woven materials which can be formed using any suitable weave pattern known in the art.

The porous surface can be that of a graft, sheath, cover, patch, sleeve, wrap, casing, and the like. These types of articles can function as the medical article itself or be used in conjunction with another part of a medical article (examples of which are described herein).

In some methods of use, matrix formation is carried out in situ, such as at a target tissue site wherein the matrix-forming components set up to form a gel. The matrix forming composition can be delivered to the target tissue site using a delivery conduit.

In some modes of practice, a catheter or microcatheter can be used to deliver the matrix forming materials to a target site. Microcatheters generally have very small diameters, such as about 5 french (fr) or less. ("French size" generally refers to units of outer diameter of a catheter; Fr size X 0.33=outer diameter of the catheter in mm.) In some aspects, the target site for matrix formation is within the vasculature, which often dictates that very small microcatheters be used, for example having a size of about 2.3 french or less, such as in the range of about 1.7 french to about 2.3 french (commercially available from, for example, Boston Scientific Excelsior SL-10 #168189). Compositions of the present invention can be can be delivered though microcatheters of these sizes at acceptable flow rates, suitable for delivering an amount of matrix forming material to the target site.

In practice, a dual lumen microcatheter can be inserted into the vasculature of a subject and navigated to place the distal end of the microcatheter at the target site. First and second compositions that include the matrix forming materials can be delivered to and mixed within at a target site.

Compositions including the matrix-forming materials can also be delivered via larger diameter catheters. Larger diameter catheters can be used to deliver the inventive compositions to one or more portions of the urogenital system.

In some aspects, the method can be performed for the treatment of an aneurysm target site. Filling of an aneurysm with the biodegradable materials of the invention can at least stabilize the aneurysm and therefore reduce the likelihood that the aneurysm will rupture of further increase in size.

Generally, following formation or placement in the body, the biodegradable matrix will erode at its surface. Since the matrix is at least partially formed from polymeric segments including poly-α(1→4)glucopyranose, degradation of the matrix in vivo can occur by enzymatic degradation of the poly-α(1→4)glucopyranose on the surface of the matrix. Enzymatic degradation of the poly-α(1→4)glucopyranose-based matrix results in the release of the naturally occurring monosaccharide glucose, which is a common serum components. This is advantageous for use of the matrices of the present invention in the body.

A carbohydrase contacts the poly-α(1→4)glucopyranose-based matrix causing enzymatic degradation of the poly-α(1→4)glucopyranose segments of the matrix. Carbohydrases that are specific for poly-α(1→4)glucopyranose are α-amylases. Serum concentrations for amylase are estimated to be in the range of about 50-100 U per liter, and vitreal concentrations also fall within this range (Varela, R. A., and Bossart, G. D. (2005) J Am Vet Med Assoc 226:88-92).

Degradation of the matrix can be increased by contacting the matrix with supplemental carbohydrase (e.g., a greater amount of carbohydrase than what is typically included produced by the body). For example, a carbohydrase can be administered to a subject, or a carbohydrase can be associated with the matrix, or a device which the matrix is associated with, wherein the carbohydrase is released from the portion and locally causes the degradation of the coating.

Example 1

Synthesis of Maltodextrin-Hydrazide

Into an amber vial, maltodextrin (5.00 g, 30.84 mmol) was weighed and dissolved into anhydrous dimethylsulfoxide (DMSO) (20.0 mL). The activating agent, 1,1'-carbonyldiimidazole (CDI) (2.50 g, 15.42 mmol) was weighed and dissolved into 25 mL DMSO. The CDI solution was pipetted slowly into the vial containing the maltodextrin, and the activation was allowed to proceed for twenty minutes at room temperature while stirring magnetically. At that time, anhydrous hydrazine (9.68 mL, 308.38 mmol) was added via syringe to the CDI/maltodextrin reaction solution. The reaction was allowed to proceed for 2-3 hours. Upon completion, the solution was diluted into deionized water and placed in Spectra/Por MWCO 1000 dialysis tubing (VWR International). Dialysis in deionized water proceeded for 36 hours. The product was removed from the tubing and lyophilized to white powder. A TNBS amine assay showed a loading level of 1.3 mmol hydrazide per gram polymer.

Example 2

Synthesis of Maltodextrin-Succinyl-Hydrazide

Into an amber vial, maltodextrin as described in Example 1 (3.00 g, 18.5 mmol) was weighed and dissolved into anhydrous DMSO (12 mL). The activating agent, 1,1'-carbonyldiimidazole (CDI) (1.50 g, 9.25 mmol) was weighed and dissolved into 25 mL DMSO. The CDI solution was pipetted slowly into the vial containing the maltodextrin and the activation was allowed to proceed for 25 minutes at room temperature while stirring magnetically. At the same time, succinic dihydrazide (13.52 g, 95.5 mmol) was solubilized into 80 mL of deionized water. The succinic dihydrazide solution was stirred at 55° C. for 25 minutes. When activation was complete, the succinic dihydrazide solution was poured into the CDI/maltodextrin solution and was allowed to react for two hours. When complete, the solution was dialyzed against deionized water in Spectra/Por MWCO dialysis tubing for 36 hours. The material was lyophilized to obtain the final white powder product. Proton NMR showed a loading of 1.548 mmol succinic hydrazide per gram of maltodextrin.

Example 3

Synthesis of Poly(Ethylene Glycol)$_{3350}$-Disuccinyl-Hydrazide

Into an amber vial, poly(ethylene glycol)$_{3350}$ (5.00 g, 1.49 mmol; PEG$_{3350}$) was dissolved into 25 mL of anhydrous tetrahydrofuran (THF). CDI (0.81 g, 5 mmol) that was predissolved into 5 mL THF was added very slowly to the PEG$_{3350}$ solution. The activation was allowed to proceed for 2.5 hours at room temperature while stirring magnetically. At that time, succinic dihydrazide (4.36 g, 29.8 mmol) was dissolved into 90 mL of 200 mM sodium acetate buffer pH 5.8. The succinic dihydrazide solution was added to the CDI/PEG$_{3350}$ solution and reaction was allowed to proceed overnight. Purification was performed by placing the product into Spectra/Por MWCO 1000 dialysis tubing. The product was dialyzed against deionized water for two days. The clear solution was removed from the tubing and lyophilized to a white fluffy solid. The product was stored at 4° C. Structural analysis was performed using $^1$H-NMR in deuterated chloroform (CdCl$_3$). Results indicated that the PEG$_{3350}$ was fully derivatized with succinic hydrazide groups (two hydrazide groups per one molecule PEG$_{3350}$).

Example 4

Synthesis of Maltodextrin-Adipyl-Hydrazide

Into an amber vial, maltodextrin as described in Example 1 (2.00 g, 12.3 mmol) was weighed and dissolved into 15 mL anhydrous DMSO. Separately, adipic dihydrazide (10.74 g, 61.7 mmol) was dissolved into 35 mL DMSO with 15 mL deionized water. The adipic dihydrazide solution was stirred at 50° C. for two hours to help dissolve the material. The adipic dihydrazide solution remained milky white. CDI (1.00 g, 6.17 mmol) was dissolved into 8 mL DMSO and placed into the maltodextrin solution. Activation of maltodextrin was allowed to proceed for 20 minutes. The maltodextrin solution was poured into the adipic dihydrazide solution slowly. The reaction proceeded at 55° C. stirring magnetically overnight. Purification by dialysis against deionized water was performed using Spectra/Por MWCO 1000 dialysis tubing. Dialysis was performed for two days. Upon completion, the product was lyophilized to obtain a fluffy white powder. $^1$H-NMR was used to determine the loading level of the adipic dihydrazide using d$_6$DMSO. The loading level was found to be 0.792 mmol adipic dihydrazide per gram of final polymer.

Example 5

Synthesis of Maltodextrin-Aldehyde Using the Periodate Method

Into an amber vial, maltodextrin as described in Example 1 (5.00 g, 30.8 mmol) was dissolved into 0.05M sodium acetate buffer pH 5.0 (30 mL). The solution was cooled to 5-10° C. for 15 minutes. A fresh solution of 0.45M sodium periodate was made immediately before use in an amber jar and cooled to 5-10° C. as well. The cooled periodate solution (17.1 mL, 7.71 mmol) was slowly poured into the cooled maltodextrin solution. The reaction remained in an ice bath for two hours while stirring magnetically. At the end of that time, the reaction solution was quenched with 3 mL ethylene glycol. To purify, the crude solution was poured into Spectra/Por MWCO 1000 dialysis tubing and dialyzed against deionized water for two days. The purified solution was lyophilized to obtain a white powder.

Example 6

Synthesis of Maltodextrin-Aldehyde Using TEMPO-Mediated Oxidation

A buffer was made containing 0.5M NaHCO$_3$ and 0.05M K$_2$CO$_3$. Approximately 125 mL of the buffer was mixed with 125 mL of DMSO. Into an amber vial, maltodextrin as described in Example 1 (10.00 g, 61.7 mmol) was dissolved into the DMSO/buffer mixture. TEMPO (2,2,6,6-tetramethyl piperidinyloxy, free radical) 0.96 g, 6.17 mmol) and tetrabutylammonium chloride (TBAC1) (1.71 g, 6.17 mmol) were added to the maltodextrin/DMSO/buffer and dissolved. N-chlorosuccinimide (NCS) (10.29 g, 77 mmol) was added to the maltodextrin solution very slowly to minimize exothermic conditions. The reaction proceeded for 3 hours at room temperature. Purification was performed by dialyzing the solution against deionized water in Spectra/Por MWCO 1000 dialysis tubing for 36 hours. The final product was lyophilized to obtain a white fluffy powder. No further analysis was performed.

Example 7

Synthesis of Poly(Ethylene Glycol)-Disuccinyl-Hydrazide

Into an amber vial, poly(ethylene glycol)$_{540}$ (2.00 g, 3.70 mmol; PEG$_{540}$) was fully dissolved into 10 mL of anhydrous tetrahydrofuran (THF). CDI (1.50 g, 9.25 mmol) that was pre-dissolved into 5 mL THF was added very slowly to the PEG$_{540}$ solution. The activation was allowed to proceed for 2.5 hours at room temperature while stirring magnetically. At that time, succinic dihydrazide (5.41 g, 37.0 mmol) was dissolved into 90 mL of 200 mM sodium acetate buffer pH 5.8. The succinic dihydrazide solution was added to the $PEG_{540}$/CDI solution and reaction was allowed to proceed overnight. Purification was performed by placing the product into Spectra/Por MWCO 500 dialysis tubing. This was dialyzed against deionized water for two days. The clear solution was removed from the tubing and lyophilized to a white fluffy solid. The product was stored at 4° C. Structural analysis was performed using $^1$H-NMR in deuterated chloroform ($CdCl_3$). Results indicated that the $PEG_{540}$ was fully derivatized with succinic hydrazide groups.

Using the same method as for the synthesis of poly(ethylene glycol)$_{540}$-disuccinic hydrazide, poly(ethylene glycols) having starting molecular weights of 1000, 1500, 2000, and 3350 were reacted with succinic dihydrazide following activation with CDI to provide succinic dihydrazide derivatives.

Example 8

Synthesis of Poly(Ethylene Glycol)$_{3350}$-Hydrazide

Into an amber vial, $PEG_{3350}$ (10.00 g, 2.99 mmol) as described in Example 3, was fully dissolved into 100 mL of anhydrous tetrahydrofuran (THF). CDI (1.06 g, 6.57 mmol) that was pre-dissolved into 5 mL THF was added very slowly to the $PEG_{3350}$ solution. The activation was allowed to proceed for 2.5 hours at room temperature while stirring magnetically. At that time, hydrazine (1.4 mL, 44.8 mmol) was dissolved into 90 mL of 200 mM sodium acetate buffer pH 5.8. The hydrazine solution was added to the $PEG_{3350}$/CDI solution and reaction was allowed to proceed overnight. Purification was performed by placing the product into Spectra/Por MWCO 1000 dialysis tubing. This was dialyzed against deionized water for two days. The clear solution was removed from the tubing and lyophilized to a white fluffy solid. The product was stored at 4° C. The predicted level of derivatization is 2 hydrazides per molecule.

Using the same method as for the synthesis of poly(ethylene glycol)$_{3350}$-hydrazide, poly(ethylene glycols) having starting molecular weights of 540, 1000, 1500, and 2000 were reacted with hydrazine following activation with CDI to provide hydrazide derivatives.

Example 9

Maltodextrin Matrix

Maltodextrin-succinyl hydrazide from Example 2 was dissolved into deionized water at 250 mg/mL. Maltodextrin aldehyde from Example 5 was also dissolved into water at 250 mg/mL. The two solutions were pipetted together at a 1:1 ratio onto a glass plate where they polymerized immediately upon contact. The gel was strong and clear.

Example 10

PEG$_{2000}$-Maltodextrin Matrix

PEG$_{2000}$-succinyl hydrazide was dissolved into deionized water at 500 mg/mL. The maltodextrin aldehyde from Example 5 was also dissolved into water at 500 mg/mL. The two solutions were pipetted together to mix adequately at a 1:1 ratio onto a glass plate. A clear and fairly uniform gel formed with bubbles present.

Example 11

Maltodextrin Matrix

Maltodextrin-hydrazide from Example 1 was dissolved into deionized water at 500 mg/mL. Maltodextrin aldehyde from Example 5 was also dissolved into water at 500 mg/mL. The two solutions were pipetted together at a 1:1 ratio onto a glass plate where they polymerized immediately upon contact, resulting in a slightly hazy gel due to inability to adequately mix the rapidly polymerized composition. Lowering the concentration of the maltodextrin-based reagents in solution, and mixing the reagents in a dual-barrel syringe system allowed for more uniform gels. Gels made from these reagents, either by pipetting or through dual-barrel delivery, form very hard matrices.

Example 12

Maltodextrin Matrix

Maltodextrin-adipo-hydrazide from Example 4 was dissolved into deionized water at 250 mg/mL. Maltodextrin aldehyde from Example 5 was also dissolved into water at 250 mg/mL. The two solutions were pipetted together at a 1:1 ratio onto a glass plate where they polymerized immediately upon contact. The gel was clear and rubbery.

Example 13

Maltodextrin-L-glutamyl-γ-hydrazide

Into an amber vial, maltodextrin (3.00 g, 18.5 mmol) is dissolved into anhydrous DMSO (12 mL). The activating agent, 1,1'-carbonyldiimidazole (CDI) (1.50 g, 9.25 mmol) is dissolved into 25 mL DMSO. This solution is pipetted slowly into the maltodextrin jar and activation proceeds for 25 minutes at room temperature while stirring magnetically. At the same time, L-glutamic acid γ-hydrazide (1.49 g, 9.25 mmol) is solubilized into 15 mL of deionized water. The solution is stirred at 55° C. for 25 minutes. When activation is complete, the L-glutamic acid γ-hydrazide is poured into the maltodextrin solution and stirred for two hours at room temperature. When complete, the solution is dialyzed against deionized water in Spectra/Por MWCO dialysis tubing for 36 hours. The material is then lyophilized.

Example 14

DNA and siRNA Release from Maltodextrin Matrices gWiz-GFP plasmid DNA (5757 bps, Aldevron, Fargo, N. Dak.) was labeled with a Cy-3 fluorescent tag using the Label-IT® reagent (Mirus Bio, Madison, Wis.). Cy-3 labeled 21 base pair siRNA was purchased from Ambion (Austin, Tex.). Hydrazide Maltodextrin-hydrazide (MD-Hyd) as described in Example I was dissolved in water at 100 or 200 mg/mL. Maltodextrin-aldehyde (MD-Ald) as described in Example 5 was dissolved in water at 50 or 100 mg/mL. 100 μL of MD-Ald solution was added to the cap of a microcentrifuge tube and mixed with 50 μg (10 μl) of fluorescently labeled plasmid DNA or 50 pmoles (10 μl) of fluorescently labeled siRNA. 100 μL of MD-Hyd was added and mixed by pipetting, and solutions were allowed to gel for 10 minutes resulting in gels with a final concentration of 50/25 or 100/50 mg/ml of MD-Hyd/MD-Ald.

Gels were then placed in 1 mL of phosphate buffered saline (PBS) with or without 23,000 U/L of porcine amylase (Sigma, St. Louis, Mo.). At designated time points, the solution was completely removed and replaced with fresh solution. The amount of released nucleic acid was determined using a fluorescent plate reader with excitation at 544 nm and emission at 590 nm.

Figure 2:
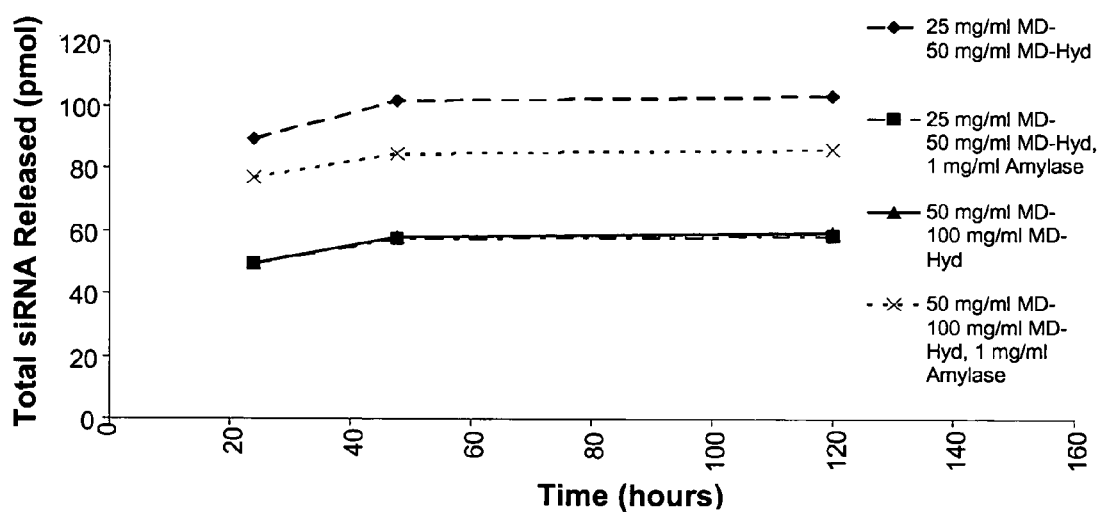
FIG. 2 is a graph showing release of siRNA from maltodextrin-based matrices over time.

Release results for DNA and siRNA respectively are shown in FIGS. 1 and 2 below. The release rate of plasmid DNA was found to be dependent on both the concentration of MD and the presence of amylase. Relatively little plasmid DNA was released or eluted from gels in the absence of amylase. However, in the presence of amylase, plasmid DNA release was gradual, and faster release was observed in the gel made using lower concentrations of MD-Hyd/MD-Ald Release of siRNA was rapid, with near complete release by 24 hours regardless of MD concentration or amylase. Released DNA and siRNA was found to be intact using agarose or polyacrylamide electrophoresis respectively.

Example 15

Maltodextrin Matrices

Three amine-reactive small molecule crosslinkers were reacted with MD-Hyd to form hydrogels. All crosslinkers were purchased from Pierce Biotechnology (Rockford, Ill.). B-[Tris(hydroxymethyl)phosphino] propionic acid (THPP, MW=196 Da) is a tri-functional crosslinker which reacts with primary and secondary amines. Dimethyl adipimidate (DMA, MW=245 Da) is a bifunctional imidoester which reacts with amino groups. Bis [sulfosuccinimidyl] suberate ($BS^3$, MW=572 Da) is a bifunctional NHS-ester which reacts with primary amines. MD-Hyd as described in Example 1 was dissolved in phosphate buffered saline (PBS, pH 7.4) at 500 mg/mL. THPP, DMA and $BS^3$ were dissolved in PBS at 50 mg/mL. 100 μL of MD-Hyd was added individually to 100 μL of each crosslinker solution in a microcentrifuge cap and mixed by pipetting. This resulted in the formation of stable gels within 10 minutes for all crosslinkers.

Example 16

DNA Release from Maltodextrin Matrices

Figure 3:
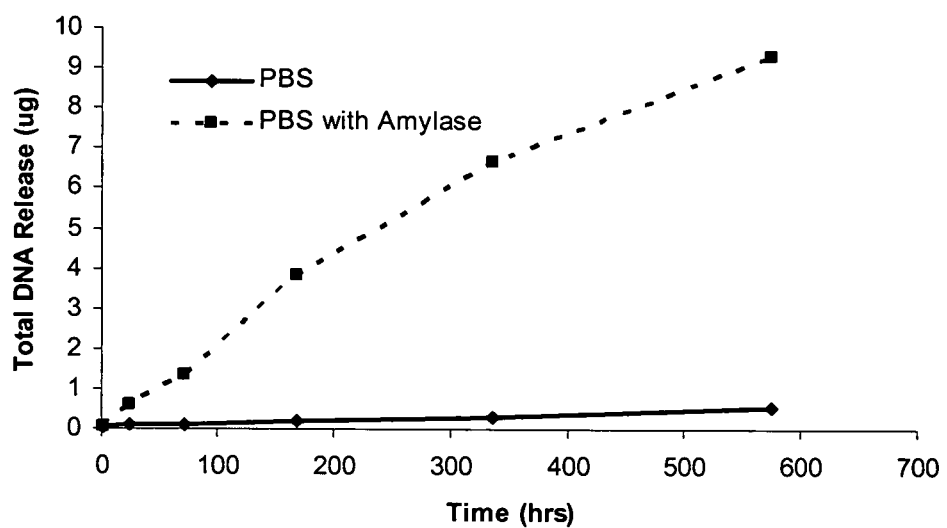
FIG. 3 is a graph showing release of plasmid DNA from maltodextrin-based matrices over time.

Reagents as described in Examples 1, 5, 14 and 15 were used in the present example. MD-Hyd (100 mg) and plasmid DNA (120 μg) were dissolved in 180 μL PBS. 20 uL of THPP at 500 mg/mL in PBS was mixed with the MD-Hyd/DNA solution by vortexing. The mixed solution was then transferred to a plastic plate in 2×100 μL aliquots and allowed to gel for 10 minutes. Each 100 μl gel was then sectioned into 4 pieces resulting in 25 uL gels with MD-Hyd at a concentration of approximately 500 mg/mL, and 15 μg plasmid DNA. Gels were then placed in 200 μL of PBS with or without porcine amylase at 1600 U/L. At select time points elution buffer was removed and replaced with fresh buffer. The amount of plasmid DNA in eluents was measured by mixing equal volumes of eluent and a solution of 1 μg/mL ethidium bromide and reading on a fluorescent plate reader with excitation at 535 nm and emission at 605 nm. Results are shown in FIG. 3. Very little plasmid DNA was released from gels which were not exposed to amylase. Gels incubated in amylase demonstrated zero order release of plasmid DNA out to 24 days.

Example 17

Polyplex DNA Release from Maltodextrin Matrices

Reagents as described in examples 1, 5, 14 and 15 were used in the present example. Polyethyleneimine (PEI, 25 kDa, branched) was obtained from Sigma (St. Louis, Mo.). MD-Hyd as described in Example 1 was dissolved in PBS (pH=7.4) at 1000 mg/mL. PEI/DNA polyplexes were prepared by combining equal volumes of Cy-3 labeled DNA in $H_2O$ with PEI in $H_2O$ to generate a mixture containing 10 μg/ml of DNA and 6 μg/mL of PEI. Polyplexes were then centrifuged under vacuum to a final concentration of 1 mg/mL DNA and 600 μg/mL PEI. 5 mg of DMA or $BS^3$ was dissolved in 60 μL of polyplex solution and then mixed with 60 μL of MD-Hyd to generate hydrogels. These gels were then sectioned into 6 equal pieces resulting in gels with a final concentration of 500 mg/mL MD-Hyd and 10 ug of polyplexed DNA. Gels were then placed in 500 μL of PBS with or without porcine amylase at 0.07 mg/mL. At select time points buffer was removed and replaced with fresh buffer. The amount of released polyplex DNA was measured using a fluorescent plate reader with excitation at 544 nm and emission at 590 nm.

Figure 4:
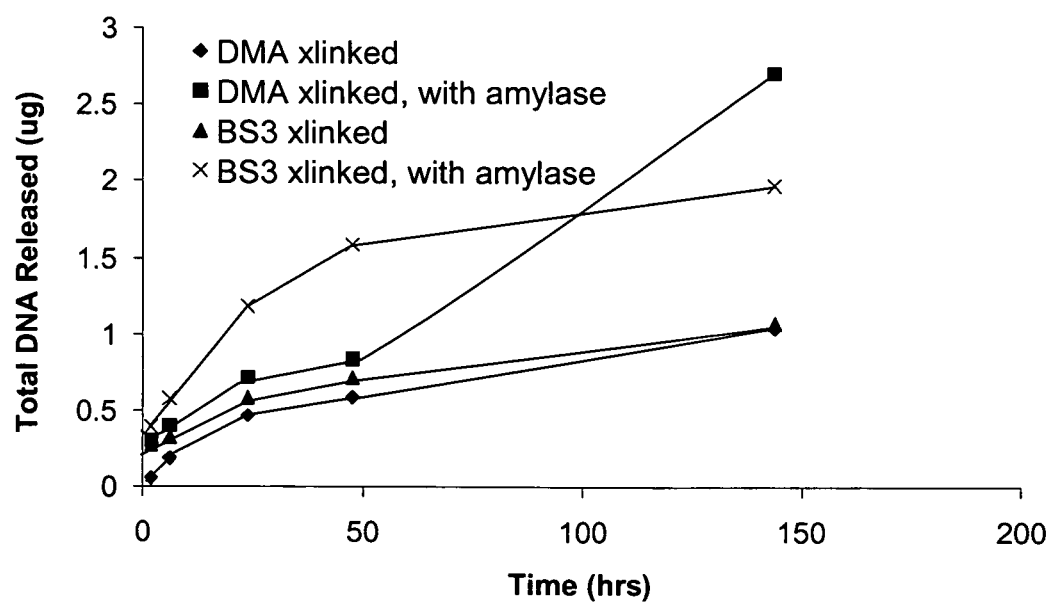
FIG. 4 is a graph showing release of polyplexed DNA from maltodextrin-based matrices over time.

Results for polyplex release are shown in FIG. 4. In gels placed in release buffer without amylase there was a slow release of polyplex for both DMA and $BS^3$ crosslinked gels. In the presence of amylase release was greater than that seen without enzyme at all time points for $BS^3$ crosslinked gels and at 144 hours for DMA crosslinked gels.

Example 18

Formation and Properties of Maltodextrin Matrices

Maltodextrin-hydrazide from Example 1 was dissolved into PBS to provide solutions of the following concentrations: 100 mg/mL and 200 mg/mL. Maltodextrin aldehyde from Example 5 was also dissolved into PBS to provide solutions of the following concentrations: 100 mg/mL, 200 mg/mL, and 400 mg/mL. The solutions were sterile filtered through a 0.45 um syringe filter.

Maltodextrin-hydrazide and maltodextrin aldehyde solutions were then mixed together to a total volume of 100 uL. Polymerization time was determined by recoding the initial time to form a viscous solution followed by shape retention and finally time to a firm matrix. Firmness was determined empirically and compared to firmness of a solution (0), fibrin hydrogel (1), or a collagen hydrogel (2). The ratio refers to the volume of each component (e.g., for 2:1 40 uL of MD-ald was mixed with 20 uL of MD-hyd). The results are shown in Table 1.

TABLE 1

| Matrix-forming reagents | Time until viscous | Firmness | Time until firm | Time until retains shape | Observations |
| --- | --- | --- | --- | --- | --- |
| 1:1 MD-ald (100 mg/ml):MD-hyd (100 mg/ml) | ~5 min | 1 | ~9 min | >7 min | opaque |
| 1:1 MD-ald (200 mg/ml):MD-hyd (200 mg/ml) | <1 min | 2.5 | ~8 min | 2 min | clear |
| 2:1 MD-ald (200 mg/ml):MD-hyd (200 mg/ml) | <1 min | 3 | ~8 min | 2 min | clear |

TABLE 1-continued

| Matrix-forming reagents | Time until viscous | Firmness | Time until firm | Time until retains shape | Observations |
|---|---|---|---|---|---|
| 1:1 MD-ald (200 mg/ml):MD-hyd (400 mg/ml) | <1 min | 2.5 | ~9 min | 2 min | clear |
| 3:1 MD-ald (200 mg/ml):MD-hyd (200 mg/ml) | <1 min | 2.1 | ~8 min | 2 min | clear |
| 3:1 MD-ald (200 mg/ml):MD-hyd (400 mg/ml) | <1 min | 2.6 | ~8 min | 3 min | clear |

Notes:
Firmness measured on a scale of 0-3 with 0 being liquid, 2 being a fibrin hydrogel, and 3 being crosslinked collagen Example 19

Amylase Degradation of Maltodextrin Matrices

Degradation studies were performed to understand the degradation rates of maltodextrin matrices formed from maltodextrin-hydrazide and maltodextrin-aldehyde materials.

A maltodextrin matrix (total volume of 60 uL) was formed using maltodextrin-hydrazide and maltodextrin aldehyde at a 1:1 mass ratio. Maltodextrin-hydrazide from Example 1 was dissolved into PBS at 200 mg/mL. The maltodextrin aldehyde from Example 5 was also dissolved into PBS at 200 mg/mL. 30 μL of each maltodextrin-based solution was combined and mixed to form a gel.

Another maltodextrin matrix (total volume of 60 uL) was formed using maltodextrin-hydrazide and maltodextrin aldehyde at a 1:2 mass ratio. Maltodextrin-hydrazide from Example 1 was dissolved into PBS at 200 mg/mL. The maltodextrin aldehyde from Example 5 was also dissolved into PBS at 200 mg/mL. Forty μL of maltodextrin-aldehyde based solution was combined with 20 ul of maltodextrin-hydrazide based solution and mixed to form a gel.

Figure 5:
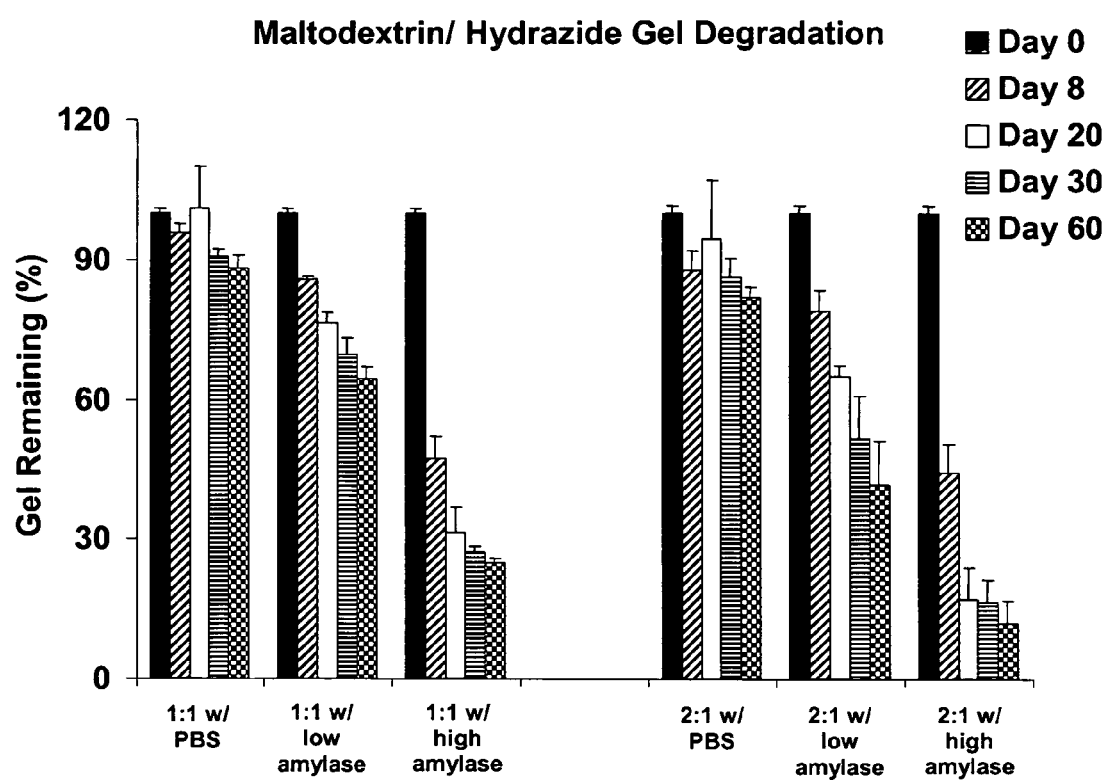
FIG. 5 is a graph showing degradation of maltodextrin-based matrices over time.

The formed gels were then placed in microeppendorf tubes for degradation studies using amylase. Porcine amylase solutions were prepared in PBS at low concentrations (920 U/L) and high concentrations (23,000 U/L). 500 μL of the amylase solutions were individually added to the tubes and incubated at 37° C. The amylase solutions were replaced three times per week and samples were collected at days 0, 8, 20, 30, and 60. Samples were then speed vacuumed, dried in a dry room, and total remaining mass of the gels was determined. For controls, the maltodextrin gels were placed in PBS, without amylase. Results of the degradation study are shown in FIG. 5.

Example 20

Maltodextrin Matrix-Based Cell Scaffold

Maltodextrin-based reagents were reacted in the presence of cells to provide biodegradable cell scaffolds.

Maltodextrin-hydrazide from Example 1 was dissolved into PBS at 200 mg/mL. Maltodextrin aldehyde from Example 5 was also dissolved into PBS at 200 mg/mL. The solutions were sterile filtered through a 0.45 um syringe filter.

Compositions containing human chondrocytes (HC) (Cell Applications, San Diego, Calif.) or human dermal fibroblasts (HDF) (Cell Applications) were prepared in maltodextrin-aldehyde at a concentration of $1.25 \times 10^6$ cells per mL.

The chondrocytes and fibroblasts were entrapped in individual matrices by resuspending centrifuged cells in maltodextrin-aldehyde to yield $1.25 \times 10^6$ cells per mL (50,000 cells in 40 ul). The maltodextrin-aldehyde/cell mixture was then plated into wells of a 96-well plate at 40 ul per well. Each well was mixed with 20 ul of the maltodextrin-hydrazide solution, for a total volume of 60 uL, to promote matrix formation. Early observations confirmed an even distribution of cells throughout the matrix. Each gel contained approximately 50,000 cells.

Figure 6:
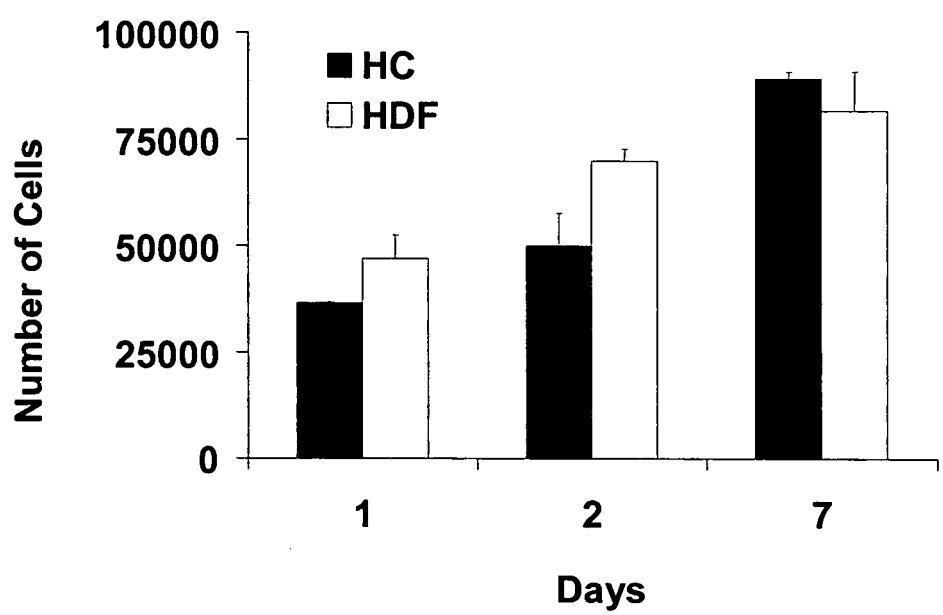
FIG. 6 is a graph showing number of human chondrocytes (HC) and human dermal fibroblasts (HDC) present in maltodextrin-based matrices at certain time points.

30 minutes following polymerization 200 uL of cell culture media (Fibroblast Growth Media and Chondrocyte Growth Media, Cell Applications) was added to each matrix and the plate was incubated at 37° C. Total cell number and viability was determined by CyQuant (Invitrogen) according to manufactures protocols on days 1, 2, and 7 and is shown in FIG. 6. Viability was assessed by a non-quantitative viability stain (Invitrogen) and was recorded at >90% (data not shown).

Example 21

Maltodextrin Matrix-Based Cell Scaffold with Photo-Protein Modification

Maltodextrin-based reagents and photo-matrix proteins were reacted to form biodegradable matrices with the matrix proteins bonded to the matrix materials via reacted photo-groups. The matrices were then seeded with cells to provide cell scaffolds.

Maltodextrin-hydrazide from Example 1 was dissolved into PBS at 200 mg/mL. Maltodextrin aldehyde from Example 5 was also dissolved into PBS at 200 mg/mL. The solutions were sterile filtered through a 0.45 um syringe filter.

Photo-collagen and photo-RGD were prepared as described in Example 1 of U.S. Pat. No. 5,744,515. Photo-RGD was prepared as described in Example 1 of U.S. Pat. No. 6,121,027. The final concentrations of photo-collagen and photo-RGD for use on the maltodextrin mixtures were 10 μg/mL, 100 μg/mL, 500 μg/mL, and 1000 μg/mL. Forty microliters of maltodextrin-hydrazide solution was added to each well. Twenty microliters of maltodextrin-hydrazide was then pipetted in and mixed to initiate matrix formation. Gels were allowed to set up for twenty minutes. 100 μL of the photo-RGD or photo-collagen was added on top of each well and illuminated for 60 seconds in the refrigerated chamber with a Dimax (365 nm) lamp. During illumination, the plates were 7.5 inches from the bottom of the lamp housing.

Next the gels were washed with PBS and then top seeded with 5000 cell/gel (with cells suspended in 200 μL of media/well) of Human chondrocytes (HC) (Cell Applications) or human dermal fibroblasts (HDF) (Cell Applications). After 2 hours of incubation at 37° C., media was changed to remove unattached cells.

Figure 7:
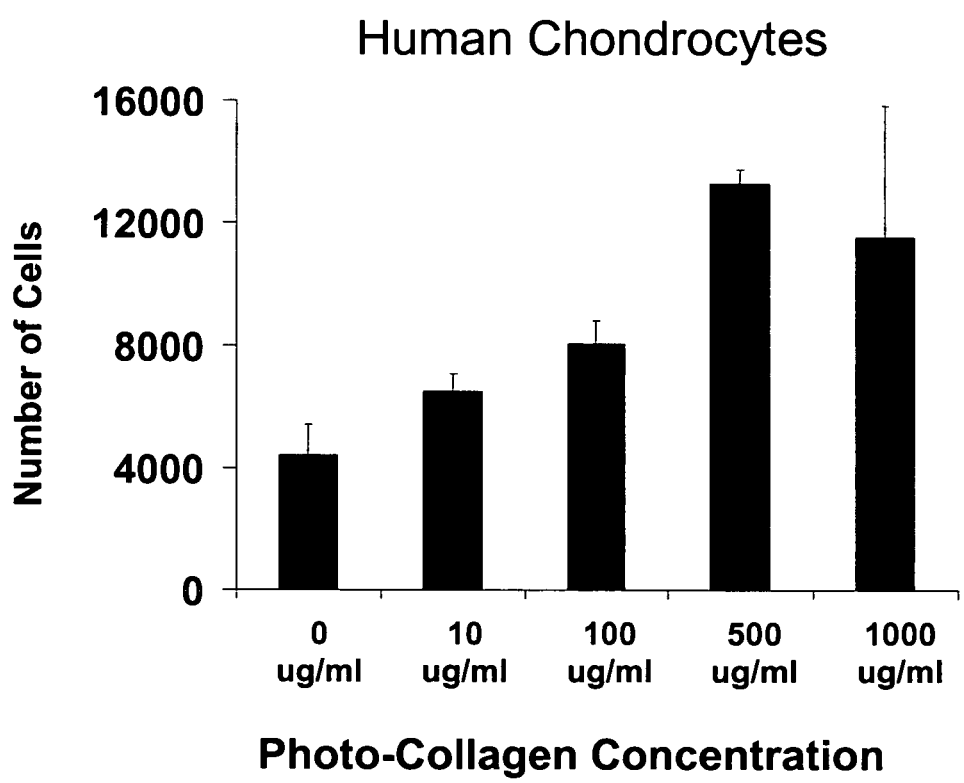
FIG. 7 is a graph showing number of human chondrocytes present in maltodextrin-based matrices derivatized with varying concentrations of photo-collagen.
Figure 8:
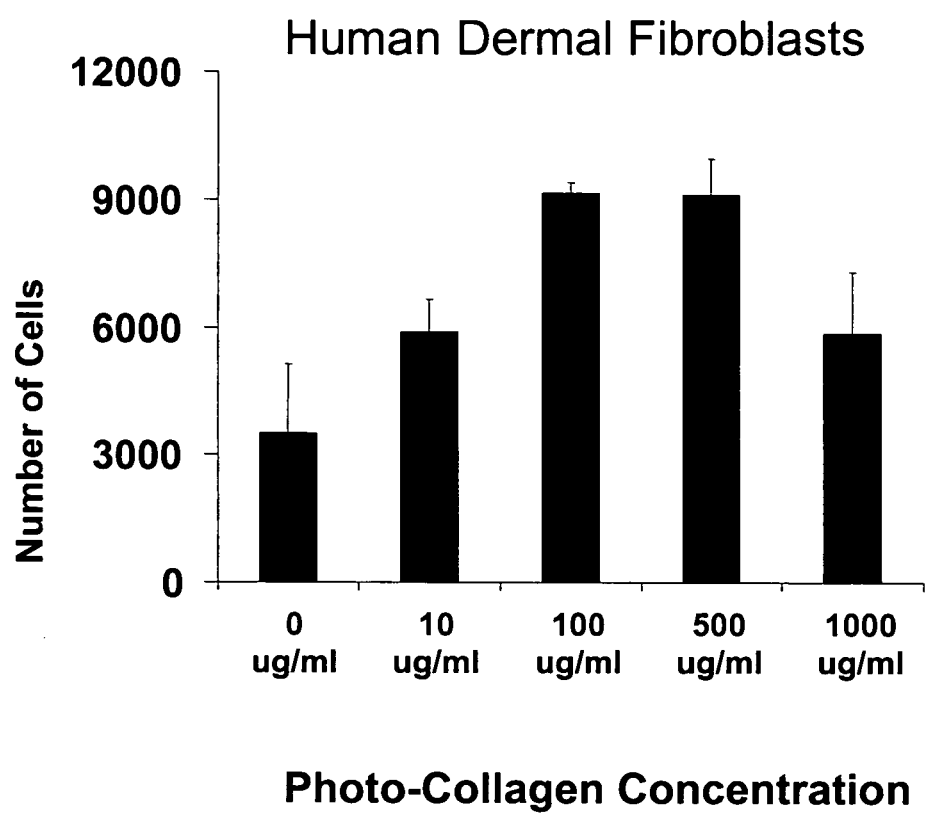
FIG. 8 is a graph showing number of human dermal fibroblasts present in maltodextrin-based matrices derivatized with varying concentrations of photo-collagen.
Figure 9:
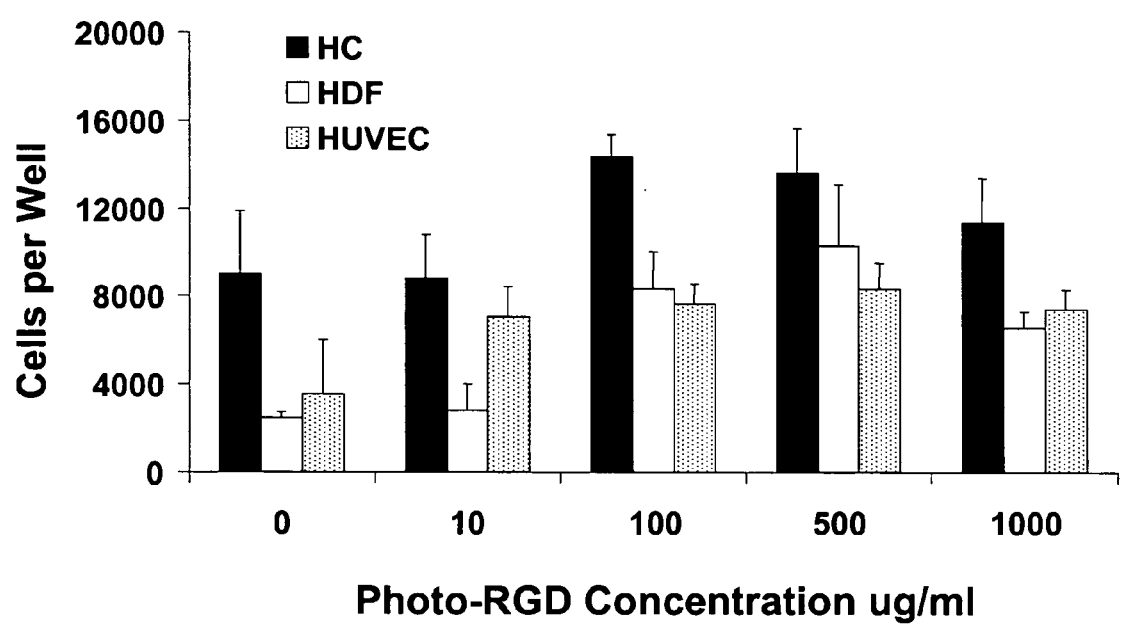
FIG. 9 is a graph showing number of human chondrocytes, human dermal fibroblasts, and human umbilical vein endothelial cells (HUVEC) present in maltodextrin-based matrices derivatized with varying concentrations of photo-RGD.
Figure 10:
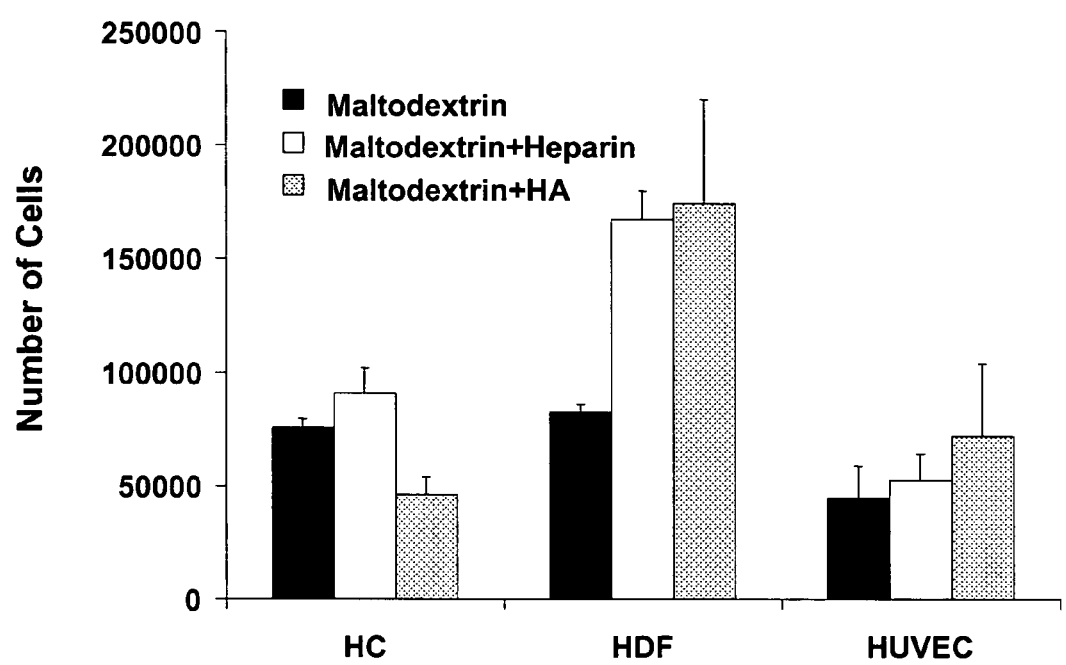
FIG. 10 is a graph showing number of human chondrocytes, human dermal fibroblasts, and human umbilical vein endothelial cells (HUVEC) present in maltodextrin-heparin or maltodextrin-hyaluronic acid based matrices.

After culture media change on each matrix, the plate was incubated at 37° C. Total cell number and viability was determined by CyQuant (Invitrogen) according to manufactures protocols on day 3. The effect of photo-RGD and photo-collagen on attachment and overall cell number was observed as increasing with the level of photo-RGD and photo-collagen concentrations as show in FIGS. 7-9.

Example 22

Maltodextrin-Heparin and Maltodextrin-Aldehyde Matrix-Based Cell Scaffold

Maltodextrin-hydrazide from Example 1 was dissolved into PBS at 200 mg/mL and Maltodextrin aldehyde from Example 5 was dissolved into PBS at 200 mg/mL. Heparin aldehyde was also dissolved into PBS at 200 mg/mL. The solutions were sterile filtered through a 0.45 um syringe filter.

Each heparin-aldehyde gel was made by mixing 20 μL of maltodextrin-aldehyde with 20 μl and heparin-aldehyde. Adding 20 μL of maltodextrin-hydrazide initiated matrix formation and then the gel was allowed to harden for 15 minutes.

Maltodextrin-hydrazide from Example 1 was dissolved into PBS at 200 mg/mL and maltodextrin aldehyde from Example 5 was dissolved into PBS at 200 mg/mL. HA aldehyde was also dissolved into PBS at 20 mg/mL. The solutions were sterile filtered through a 0.45 um syringe filter.

Each HA-aldehyde gel was made by mixing 26 μl of maltodextrin-aldehyde and 26 μl of HA-aldehyde. 8 μL of maltodextrin-hydrazide was then added to initiate matrix formation and the gel was allowed to harden for 15 minutes.

Example 23

Compression Testing

The physical properties of matrices formed from oxidized maltodextrin (prepared according to Example 5) and hydrazide-derivatized poly(ethylene glycols) (prepared according to Example 8) were determined by compression force testing and swellability testing. Compressive force of the gels was tested using a TAXT2™ texture analyzer with 5 mm diameter ball probe was used to determined compression strength. The procedure used a test speed of 0.5 mm/sec and a trigger force of 4 g. The probe compressed to 25% of the depth of the material as compared to the calibration depth. The results are shown in Table 2.

TABLE 2

| Matrix-forming reagents | Force (g) | Distance (mm) | Time (sec) |
|---|---|---|---|
| 100 mg oxidized MD-100 mg PEG 1500 hydrazide-1 | 65.1 | 0.6 | 1.2 |
| 100 mg oxidized MD-100 mg PEG 2000 hydrazide-1 | 51.1 | 0.4 | 0.9 |
| 100 mg oxidized MD-100 mg PEG 2000 succinic dihydrazide-1 | 42.2 | 0.6 | 1.2 |
| 100 mg oxidized MD-200 mg PEG 3350 hydrazide-1 | 66.9 | 0.5 | 1.0 |

What is claimed is:

1. A biodegradable, biocompatible crosslinked polymeric matrix comprising crosslinked poly-α(1→4)glucopyranose polymers and a linker between the poly-α(1→4)glucopyranose polymers having Formula IIIa, Formula IIIb, Formula IVa, or Formula IVb:

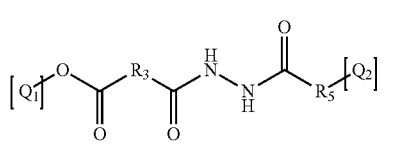

Formula IIIa

Formula IIIb

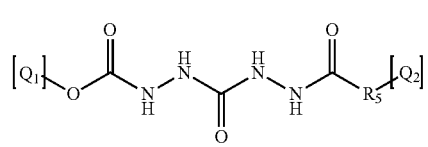

Formula IVa

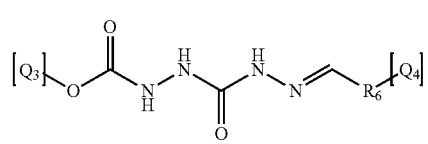

Formula IVb where, in Formula IIIa or IVa, $Q_1$ and $Q_2$ represent monomeric units of the α(1→4) glucopyranose polymers; $R_3$ is a cyclic, linear, or branched carbon-containing group, $R_5$ is O, or a cyclic, linear, or branched carbon-containing groups that contain one or more heteroatoms selected from the group of oxygen and nitrogen; or in Formula IIIb or IVb, $Q_3$ and $Q_4$ represent monomeric units of α(1-4) glucopyranose polymers, and $R_6$ is a covalent bond, or a cyclic, linear, or branched carbon-containing groups that contain one or more heteroatoms selected from the group of oxygen and nitrogen.

2. The biodegradable, biocompatible crosslinked polymeric matrix of claim 1 where, in Formula IIIa or IVa, $R_5$ is O to form an ester group in the linker.

3. The biodegradable, biocompatible crosslinked polymeric matrix of claim 1 further comprising a bioactive agent.

4. The biodegradable, biocompatible crosslinked polymeric matrix of claim 3 further comprising microparticles, wherein the microparticles comprise the bioactive agent.

5. The biodegradable, biocompatible crosslinked polymeric matrix of claim 3 wherein the bioactive agent comprises a nucleic acid and wherein the nucleic acid is associated with a carrier component to promote entry of the nucleic acid into a cell.

6. The biodegradable, biocompatible crosslinked polymeric matrix of claim 3 wherein the bioactive agent is selected from the group consisting of polypeptides, polysaccharides, or polynucleotides.

7. The biodegradable, biocompatible crosslinked polymeric matrix of claim 1 further comprising bioparticles selected from the group consisting of viral particles and cells.

8. The biodegradable, biocompatible crosslinked polymeric matrix of claim 1, wherein the matrix further comprises cell attachment factors, and cells are attached to cell attachment factors in the matrix.

9. The biodegradable, biocompatible crosslinked polymeric matrix of claim 8 wherein the cell attachment factor is selected from the group consisting of fibronectin, vitronectin, laminin A, laminin B1, laminin B2, collagen I, and thrombospondin and active portions selected from the group consisting of RGDS (SEQ ID NO:10), LDV, REDV (SEQ ID NO:13), RGDV (SEQ ID NO:12), LRGDN (SEQ ID NO:5), IKVAV (SEQ ID NO:6), YIGSR (SEQ ID NO:1), PDSGR (SEQ ID NO:8), RNIAEIIKDA (SEQ ID NO:9), RGDT (SEQ ID NO:11), DGEA (SEQ ID NO:2), GTPGPQ-GIAGQRGVV (SEQ ID NO:3), RGD, VTXG (SEQ ID NO:4), and FYVVMWK (SEQ ID NO:7).

10. The biodegradable, biocompatible crosslinked polymeric matrix of claim 8, wherein the cell attachment factors are covalently attached to the matrix via the linker segments, or are covalently attached to the matrix via a reacted group.

11. The biodegradable, biocompatible crosslinked polymeric matrix of claim 1 wherein the poly-α(1→4)glucopyranose polymeric segment is 50 wt % or greater of a total weight amount of matrix-forming solids in the matrix.

12. The biodegradable, biocompatible crosslinked polymeric matrix of claim 1 wherein the poly-α(1→4)glucopyranose is maltodextrin and wherein the matrix has a ratio of hydrazide groups (Hyd), present in the linker of formula III or IV, to maltodextrin (MD) in the range of 0.1 mmol (Hyd) per gram (MD) to about 2 mmol (Hyd) per gram (MD).

13. The biodegradable, biocompatible crosslinked polymeric matrix of claim 1 wherein in Formula IIIa or Formula IIIb, $R_3$ is a cyclic, linear, or branched carbon-containing group having 1-12 carbon atoms.

14. The biodegradable, biocompatible crosslinked polymeric matrix of claim 13 wherein in Formula IIIa or Formula IIIb, $R_3$ is a —$(CH_2)_n$— group, wherein n is from 1-12.

15. The biodegradable, biocompatible crosslinked polymeric matrix of claim 14 wherein in Formula IIIa or Formula IIIb, $R_3$ is a —$(CH_2)_n$— group, wherein n is from 2-4.

16. The biodegradable, biocompatible crosslinked polymeric matrix of claim 1 wherein in Formula IIIb or Formula IVb, $R_6$ is a covalent bond.

17. The biodegradable, biocompatible crosslinked polymeric matrix of claim 1 comprising a chemistry of Formula IVb as follows:

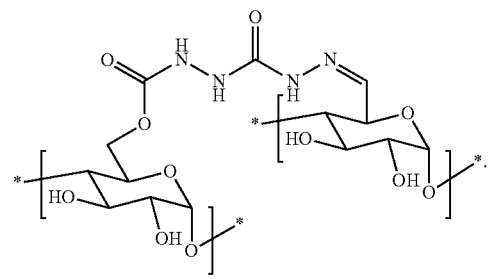

18. A system for forming a biodegradable, biocompatible crosslinked polymeric matrix the system comprising:

an α(1→4)glucopyranose polymer that comprises pendent hydrazide groups having a structure according one of Formula VI, VII, or VIII:

Formula VI

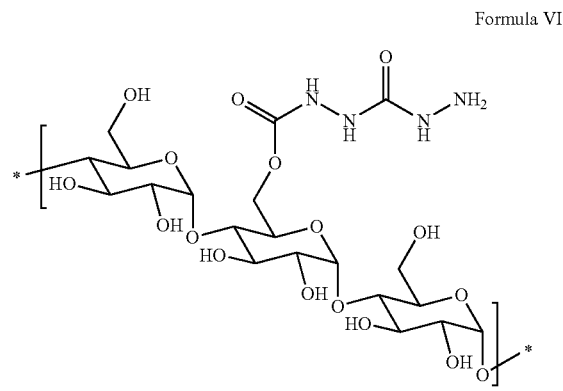

Formula VII

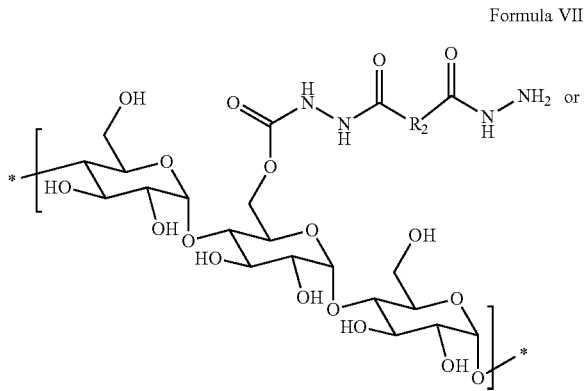

Formula VIII

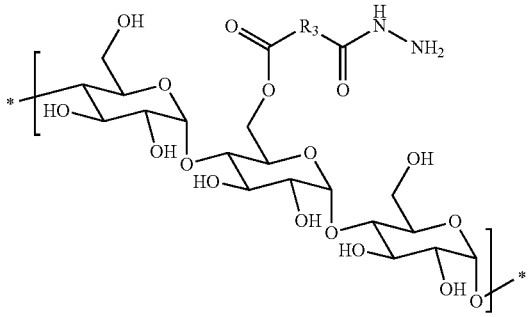

where, in formulas VII and VIII, $R_2$ and $R_3$ are cyclic, linear, or branched carbon-containing group having 1-12 carbon atoms, and a second polymer that comprises pendent hydrazide reactive groups, wherein:

the hydrazide groups have a degree of substitution on the α(1→4)glucopyranose polymer in the range of 0.05 to about 1.0, and the second polymer comprises a α(1→4)glucopyranose polymer.

19. The system of claim 18 wherein the hydrazide-reactive groups are selected from the group consisting of aldehyde, acyl halide, NHS-ester, carboxylic acid, imidazole, hydroxyl methyl phosphine, and unsaturated ester.

20. The system of claim 18 wherein the α(1→4)glucopyranose polymer has degree of substitution with the either the first or second reactive groups in the range of 0.1 to about 1.0.

21. The system of claim 18 wherein the α(1→4)glucopyranose polymer, the second polymer, or both, have a molecular weight of 500,000 Da or less.

22. The system of claim 18 where, in Formula VII or VIII, $R_2$ or $R_3$ is a —$(CH_2)_n$— group and n is from 1-12.

23. The system of claim 18 wherein the second polymer comprises a α(1→4)glucopyranose polymer comprising pendent aldehyde groups.

24. A method for forming a biodegradable, biocompatible crosslinked polymeric matrix the system comprising at step of:

contacting α(1→4)glucopyranose polymer that comprises pendent hydrazide groups having a structure according one of Formula VI, VII, or VIII according to claim 18 with a second component that comprises hydrazide-reactive groups, wherein the hydrazide groups have a degree of substitution on the α(1→4)glucopyranose polymer in the range of 0.05 to about 1.0, and wherein the second component comprises a α(1→4)glucopyranose polymer.

25. The method of claim 24 wherein the step of contacting is performed in an aqueous composition and the α(1→4)glucopyranose polymer and the second component are included in a total amount in the range of 20 mg/mL to about 500 mg/mL.

26. The method of claim 24 wherein the step of contacting is performed in vivo or in situ.

27. A method of delivering a biodegradable, biocompatible crosslinked polymeric matrix comprising a step of placing or forming the biodegradable, biocompatible crosslinked polymeric matrix of claim 1 at a target location of a body, wherein the matrix comprises a component selected from the group consisting of cells, cell attachment factors, growth factors, cytokines, antibodies and antibody fragments, polynucleotides, microparticles comprising bioactive agent and viral particles wherein the matrix degrades over a period of time at the target location.

* * * * *